United States Patent [19]
Chantry et al.

[11] Patent Number: 5,591,618
[45] Date of Patent: Jan. 7, 1997

[54] G PROTEIN-COUPLED RECEPTOR KINASE GRK6

[75] Inventors: David Chantry; Patrick W. Gray, both of Seattle; Merl F. Hoekstra, Snohomish, all of Wash.

[73] Assignee: ICOS Corporation, Bothell, Wash.

[21] Appl. No.: 454,439

[22] Filed: May 30, 1995

Related U.S. Application Data

[60] Division of Ser. No. 221,817, Mar. 31, 1994, Pat. No. 5,532,151, which is a continuation-in-part of Ser. No. 123,932, Sep. 17, 1993, abandoned.

[51] Int. Cl.$^6$ .............................. C12Q 1/68; C12N 9/12; C12N 5/00; C07H 19/00
[52] U.S. Cl. .......................... 435/194; 435/6; 435/740.2; 435/252.3; 435/320.1; 536/22.1; 536/23.1; 536/23.2; 536/23.5
[58] Field of Search ........................... 435/6, 196, 240.2, 435/252.3, 320.1; 576/22.1, 23.1, 23.2, 23.5

[56] References Cited

FOREIGN PATENT DOCUMENTS

WO93/05182  3/1993  WIPO .

OTHER PUBLICATIONS

Benovic et al "Molecule Cloning . . . " JBC vol. 268 No. 26, pp. 19521–19527 Sep. 15, 1993.
Adams et al., "Sequence identification of 2,375 human brain genes," *Nature*, 355:632–634 (Feb. 13, 1992).
Ambrose et al., "A novel G protein–coupled receptor kinase gene cloned from 4p16.3," *Hum. Mol. Genet.*, 1:697–703 (1992).
Benovic et al., "Cloning, Expression, and Chromosomal Localization of β–Adrenergic Receptor Kinase 2," *J. Biol. Chem.*, 266:14939–14946 (Aug. 16, 1991).
Benovic et al., "β–Adrenergic Receptor Kinase: Primary Structure Delineates a Multigene Family," *Science*, 246:235–240 (Oct. 13, 1989).
Benovic et al., "Molecular Cloning and Expression of GRK6", *J. Biol. Chem.*, 268(26):19521–19527 (Sep. 15, 1993).
Bouwer et al., "Adoptive Transfer of Experimental Allergic Encephalomyelitis: Conditions Influencing Memory and Effector Cell Development," *Cellular Immunol.*, 131:219–231 (1990).
Cassill et al., "Isolation of *Drosophila* genes encoding G protein–coupled receptor kinases," *Proc. Natl. Acad. Sci. USA*, 88:11067–11070 (Dec., 1991).
Dohlman et al., "Model Systems For The Study of Seven- -Transmembrane–Segment Receptors," *Ann. Rev. Biochem.*, 60:653–688 (1991).

Erbeck et al., "Differential Uncoupling of Chemoattractant Receptors from G Proteins in Retinoic Acid–Differentiated HL–60 Granulocytes,"*J. Immunol.*, 150:1913–1921 (Mar. 1, 1993).
Erickson et al., "Macromolecular X-Ray Crystallography and NMR as Tools for Structure–based Drug Design," *Ann. Reports in Med. Chem.*, 27:271–289 (1992).
Gerard et al., "The chemotactic receptor for human C5a anaphylatoxin," *Nature*, 349:614–617 (Feb. 14, 1991).
Hanks et al., "Protein Kinase Catalytic Domain Sequence Database: Identification of Conserved Features of Primary Structure . . . ," *Meth. Enzymol.*, 200:38–62 (1991).
Haribabu et al., "Identification of additional members of human G–protein–coupled receptor kinase multigene family," *Proc. Natl. Acad. Sci. USA*, 90:9398–9402.
Holmes et al., "Structure and Functional Expression of a Human Interleukin–8 Receptor," *Science*, 253:1278–1280 (Sep. 13, 1991).
Inglese et al., "Isoprenylation of a Protein Kinase," *J. Biol. Chem.*, 267:1422–1425 (Jan. 25, 1992).
Khorana, "Rhodopsin, Photoreceptor of the Rod Cell," *J. Biol. Chem.*, 267;1–4 (Jan. 5, 1992).
Klein et al., "cAMP Induces a Rapid and Reversible Modification of the Chemotactic Receptor in *Dictyostelium discoideum,*" *J. Cell Biol*, 100:715–720 (Mar. 1985).
Koga et al., "A human T cell–specific cDNA clone (YT16) encodes a protein with extensive homology to a family of protein–tyrosine kinases," *Eur. J. Immunol.*, 16:1643–1646 (1986).
Kozak, "An Analysis of Vertebrate mRNA Sequences: Intimations of Translational Control," *J. Cell. Biol.*, 115:887–903 (Nov., 1991).
Kunapuli et al., "Cloning and expression of GRK5: A member of the G protein–coupled receptor kinase family," *Proc. Natl. Acad. Sci. USA*, 90:5588–5592 (Jun., 1993).
Kwatra et al., "Correlation of Agonist–induced Phosphorylation of Chick Heart Muscarinic Receptors with Receptor Desensitization," *J. Biol. Chem.*, 262:16314–16321 (Dec. 5, 1987).

(List continued on next page.)

*Primary Examiner*—Charles Patterson, Jr.
*Assistant Examiner*—Hyosuk Kim
*Attorney, Agent, or Firm*—Marshall, O'Toole, Gerstein, Murray & Borun

[57] ABSTRACT

The present invention provides purified and isolated polynucleotide sequences encoding the novel G protein-coupled receptor kinase designated GRK6. Also provided by the invention are methods and materials for the recombinant production of GRK6 enzyme and methods for identifying compounds which modulate the protein kinase activity of GRK6.

3 Claims, 13 Drawing Sheets

OTHER PUBLICATIONS

LaVallie et al., "A Thioredoxin Gene Fusion Expression System that Circumvents Inclusion Body Formation in the *E. Coli* Cytoplasm," *Biotechnology*, 11:187–193 (Feb., 1993).

Lefkowitz, "G Protein-Coupled Receptor Kinases," *Cell*, 74:409–412 (Aug. 13,1993).

Linder et al., "G Proteins," *Sci. Am.*, 267:56–65 (Jul., 1992).

Lorenz et al., "The receptor kinase family: Primary structure of rhodopsin kinase reveals similarities to the β–adrenergic receptor kinase," *Proc. Natl. Acad. Sci. USA*, 88:8715–8719 (Oct., 1991).

Maldonado et al., "A cDNA clone encoding human cAMP-dependent protein kinase catalytic subunit Cα," *Nuc. Acids. Res.*, 16:8189–8190 (1988).

Murphy et al., "Cloning of Complementary DNA Encoding a Functional Human Interleukin–8 Receptor," *Science*, 253:1280–1283 (Sep. 13, 1991).

Neote et al., "Molecular Cloning, Functional Expression, and Signaling Characteristics of a C—C Chemokine Receptor," *Cell*, 72:415–425 (Feb. 12, 1993).

Oskenberg et al., "A single amino–acid difference confers major pharmacological variation between human and rodent 5–$HT_{1B}$ receptors," *Nature*, 360:161–163 (Nov. 12, 1992).

Palczewski et al., "Identification of the N–terminal Region in Rhodopsin Kinase Involved in Its Interaction with Rhodopsin," *J. Biol. Chem.*, 268:6004–6013 (Mar. 15, 1993).

Palczewski et al., "G–protein–coupled receptor kinases," *Trends Biochem, Sci.*, 16:387–391 (Oct., 1991.)

Parker et al., "The Complete Primary Structure of Protein Kinase C—the Major Phorbol Ester Receptor," *Science*, 233:853–859 (Aug. 22, 1986).

Pippig et al., "Overexpression of β–Arrestin and β–Adrenergic Receptor Kinase Augment Desensitization of $β_2$–Adrenergic Receptors," *J. Biol. Chem.* 268:3201–3208 (Feb. 15 ,1993).

Probst et al., "REVIEW ARTICLE:: Sequence Alignment of the G–Protein Coupled Receptor Superfamily," *DNA and Cell Biol.*, 11:1–20 (1992).

Reneke et al., "The Carboxy–Terminal Segment of the Yeast α–Factor Receptor Is a Regulatory Domain," *Cell*, 55:221–234 (Oct. 21, 1988).

Schleicher et al., "A β–adrenergic receptor kinase–like enzyme is involved in olfactory signal termination," *Proc. Natl. Acad. Sci. USA*, 90:1420–1424 (Feb., 1993).

Thomas et al., "Molecular cloning of the fMet–Leu–Phe Receptor from Neutrophils," *J. Biol. Chem.*, 265:20061–20064 (Nov. 25, 1990).

| | | | | | |
|---|---|---|---|---|---|
| GRK6 | ME----LENIV | ANTVLLKARE | --GGGGNRKG | KSKKWROMLQ | FPHISQCEEL | 45 |
| GRK5 | ME----LENIV | ANTVLLKARE | --GGGGKRKG | KSKKWKEILK | FPHISQCEDL | 45 |
| IT-11 | ME----LENIV | ANSLLLKARQ | ---------- | ---------- | ---------- | 17 |
| RK | MDFGSLETVV | ANSAFIAARG | SFDASSGPAS | RDRKYLARLK | LPPLSKCEAL | 50 |
| GPRK2 | M--------- | ---------- | ---------- | ---------- | ---------- | 1 |
| BARK1 | MA--DLEAVL | ADVSYLMAME | KSKATPAARA | SKKILLPEPS | IRSVMQ-KYL | 47 |
| BARK2 | MA--DLEAVL | ADVSYLMAME | KSKATPAARA | SKKVVLPEPS | IRSVMQ-RYL | 47 |
| GPRK1 | MA--DLEAVL | ADVSYLMAME | KSKCTPAARA | SKKLNLPDPS | VRSVMY-KYL | 47 |
| | | | | | |
| GRK6 | RLSLERDYHS | LCERHRIGRL | LFREFC-ATR | PELSRCVAFL | DGVAEYE-VT | 93 |
| GRK5 | RRTIDRDYCS | LCDKQPIGRL | LFRQFC-ETR | PGLECYIQFL | DSVAEYE-VT | 93 |
| IT-11 | ----EKDYSS | LCDKQPIGRL | LFRQFC-DTK | PTLKRHIEFL | DAVAEYE-VA | 61 |
| RK | RESLDLGFEG | MCLEQPIGRR | LFQQFL-RTH | EQHGPALQLW | KDIEDYD-TA | 98 |
| GPRK2 | ---------- | ---------- | ---------- | ---------- | ---------- | 1 |
| BARK1 | EDRGEVTFEK | I-FSQKLGYL | LFRDFCLNHL | EEARPLVEFY | EEIKKYEKLE | 96 |
| BARK2 | AERNEITFDK | I-FNQKIGFL | LFKDFCLNEI | GEAVPQVKFY | EEIKEYEKLD | 96 |
| GPRK1 | EKEGELNFHK | N-FNEVLGYL | LFKDFCENDS | EEPIQQLKFF | EQIKLFEKTE | 96 |

FIGURE 1A

```
GRK6    ------    ------    ------    ------    ------     142
GRK5    PDDKRKACGR HVTQNFLSHT GPDLIPEVPR QLVTNCTQRL -EQGPCKDLF  142
IT-11   PDEKLGEKGK EIMTKYLTPK SPVFIAQVGQ DLVSQTEEKL -LQKPCKELF  142
RK      DDEDRSDCGL SILDRFFNDK LAAPLPEIPP DVVTECRLGL KEENPSKKAF  111
GPRK2   DDALRPQKAQ ALRAAYLEPQ AQLFCSFLDA ETVARAR--- --AGAGDGLF  143
BARK1   ---------- ---------- ---------- ---------- ---------    1
BARK2   TEEERVARSR EIFDSYIMKE LLACSHPFSK SATEHVQGHL GKKQVPPDLF  146
GPRK1   NEEDRLHRSR QMYDAYIMRE LLSSTHQFSK QAVEHVQSHL SKKQVTPTLF  146
        CYDERKKMAR DIYDNFIMEE MLSHTYEYSK HAVASVQKYL LKNEVPVDLF  146

GRK6    QELTRLTHEY LSVAPFADYL DSIYFNRFLQ WKWLERQ-PV TKNTFRQYRV  191
GRK5    SACAQSVHEY LRGEPFHEYL DSMFFDRFLQ WKWLERQ-PV TKNTFRQYRV  191
IT-11   EECTRVAHNY LRGEPFEEYQ ESSYFSQFLQ WKWLERQ-PV TKNTFRHYRV  160
RK      QPLLRAVLAH LGQAPFQEFL DSLYFLRFLQ WKWLEAQ-PM GEDWFLDFRV  192
GPRK2   ---------- ---------- ---YFHRYLQ WKWLEAQ-PI TYKTFRMYRV   27
BARK1   QPYIEEICQN LRGDVFQKFI ESDKFTRFCQ WKNVELNIHL TMNDFSVHRI  196
BARK2   QPYIEEICES LRGDIFQKFM ESEKFTRFCQ WKNVELNIHL SMNDFSVHRI  196
GPRK1   EPYLEEIFTQ LKGKPFKKFL ESDKFTRFCQ WKNLELNIQL TMNDFSVHRI  196
```

FIGURE 1B

| | | | | | |
|---|---|---|---|---|---|
| GRK6 | LGKGGFGEVC | ACQVRATGKM | YACKKLEKKR | IKKRKGEAMA | LNEKQILEKV | 241 |
| GRK5 | LGKGGFGEVC | ACQVRATGKM | YACKRLEKKR | IKKRKGESMA | LNEKQILEKV | 241 |
| IT-11 | LGKGGFGEVC | ACQVRATGKM | YACKKLQKKR | IKKRKGEAMA | LNEKRILEKV | 210 |
| RK | LGRGGFGEVF | ACQMKATGKL | YACKKLNKKR | LKKRKGYQGA | MVEKKILAKV | 242 |
| GPRK2 | LGKGGFGEVC | ACQVRATGKM | YACKKLEKKR | IKKRKGESMV | LIEKQILQKI | 77 |
| BARK1 | IGRGGFGEVY | GCRKADTGKM | YAMKCLDKKR | IKMKQGETLA | LNERIMLSLV | 246 |
| BARK2 | IGRGGFGEVY | GCRKADTGKM | YAMKCLDKKR | VKMKQGETLA | LNERIMLSLV | 246 |
| GPRK1 | IGRGGFGEVY | GCRKADTGKM | YAMKCLDKKR | IKMKQGEMLA | LNERNMLQAV | 246 |

| | | | | | |
|---|---|---|---|---|---|
| GRK6 | ----NSRFVV | SLAYAYETKD | ALCLVLTLMN | GGDLKFHIYH | MG-Q-AGFPE | 285 |
| GRK5 | ----NSQFVV | NLAYAYETKD | ALCLVLTIMN | GGDLKFHIYN | MG-N-PGFEE | 285 |
| IT-11 | ----QSRFVV | SLAYAYETKD | ALCLVLTIMN | GGDIRYHIYN | LG-N-PGFDE | 254 |
| RK | ----HSRFIV | SLAYAFETKT | DLCLVMTIMN | GGDIRYHIYN | VDEDNPGFQE | 288 |
| GPRK2 | ----NSPFVV | NLAYAYETKD | ALCLVLTIMN | GGDLKFHIYN | MGGE-PGFEL | 122 |
| BARK1 | STG-DCPFIV | CMSYAFHTPD | KLSFILDLMN | GGDLHYHLSQ | HG-----VFSE | 291 |
| BARK2 | STG-DCPFIV | CMTYAFHTPD | KLCFILDLMN | GGDMHYHLSQ | HG-----VFSE | 291 |
| GPRK1 | STGIDCPFIV | CMTYAFHTPD | KLCFILDLMN | GGDLHYHLSQ | HG-----IFSE | 292 |

FIGURE 1C

```
GRK6    ARAVFYAAEI CCGLEDLHRE RIVYRDLKPE NILLDDHGHI RISDLGLAVH  334
GRK5    ERALFYAAEI LCGLEDLHRE NTVYRDLKPE NILLDDYGHI RISDLGLAVK  335
IT-11   QRAVFYAAEL CCGLEDLQRE RIVYRDLKPE NILLDDRGHI RISDLGLATE  304
RK      PRAIFYTAQI VSGLEHLHQR NIIYRDLKPE NVLLDDDGNV RISDLGLAVE  338
GPRK2   ERARFYAAEV ACGLQHLHKQ GIVYRDCKPE NILLDDHGHV RISDLGLAVE  172
BARK1   ADMRFYAAEI ILGLEHMHNR FVVYRDLKPA NILLDEHGHV RISDLGLACD  341
BARK2   KEMRFYASEI ILGLEHMHTC FVVYRDLKPA NILLDEYGHV RISDLGLACD  341
GPRK1   DEMKFYAAEV ILGLEHMHKR CIVYRDLKPA NILLDENGHI RISDLGLACD  342

GRK6    VPEGQ-TIKG RVGTVGYMAP EVVKNER-YT FSPDWWALGC LLYEMIAGQS  382
GRK5    IPEGD-LIRG RVGTVGYMAP EVLNNQR-YG LSPDYWGLGC LIYEMIEGQS  383
IT-11   IPEGQ-RVRG RVGTVGYMAP EVVNNEK-YT FSPDWWGLGC LIYEMIQGHS  352
RK      LKAGQTKTKG YAGTPGFMAP ELLGEE-YD FSVDYFALGV TLYEMIAARG  387
GPRK2   IPEGE-MVRG RVGTVGYMAP EVIDNEK-YA FSPDWFSFGC LLYEMIEGQA  220
BARK1   FSKK--KPHA SVGTHGYMAP EVLQKGVAYD SSADWFSLGC MLFKLLRGHS  389
BARK2   FSKK--KPHA SVGTHGYMAP EVLQKGTCYD SSADWFSLGC MLFKLLRGHS  389
GPRK1   FSKK--KPHA SVGTHGYMAP EVLSKGTSYD SCADWFSFGC MLYKLLKGHS  390
```

FIGURE 1D

```
GRK6    PFQQRKKKIK  REEVERLVKE  VPEEYSERFS  PQARSLCSQL  LCKDPAER--  431
GRK5    PFRGRKEKVK  REEVDRRVLE  TEEVYSHKFS  EEAKSICKML  LTKDAKQR--  431
IT-11   PFKKYKEKVK  WEEVDQRIKN  DTEEYSEKFS  EDAKSICRML  LTKNPSKR--  400
RK      PFRARGEKVE  NKELKQRVLE  QAVTYPDKFS  PASKDFCEAL  LQKDPEKR--  435
GPRK2   PFRMRKEKVK  REEVDRRVKE  DPEKYSSKFN  DEAKSMCQQL  LAKSIKQR--  268
BARK1   PFRQHKTKDK  HE-IDRMTLT  MAVELPDSFS  PELRSLLEGL  LQRDVNRRLG  438
BARK2   PFRQHKTKDK  HE-IDRMTLT  VNVQLPDAFS  PELRSLLEGL  LQRDVSQRLG  438
GPRK1   PFRQHKTKDK  LE-IDKMTLT  MNVELPESFS  LELKNLLEML  LQRDVSKRLG  439

GRK6    -L--GCRGG-  -SA--REVK-  ------EH    PL--------  ----FK--KL  451
GRK5    -L--GCQEE-  -GA--AEVK-  ------RH    PF--------  ----FR--NM  451
IT-11   -L--GCRGE-  -GA--AGVK-  ------QH    PV--------  ----FK--DI  420
RK      -L--GFRDG-  -SC--DGLR-  ------TH    PL--------  ----FR--DI  455
GPRK2   -L--GCRNGR  MGG--QDVM-  ------AH    PF--------  ----FHSTQL  292
BARK1   CLGRGAQEVK  ESPFFRSLDW  QMVFLQKYPP  PLIPPRGEVN  AADAFDIGSF  488
BARK2   CYGGGARELK  EHIFFKGIDW  QYVYLRKYPP  PLIPPRGEVN  AADAFDIGSF  488
GPRK1   CMGNGADEVK  MHNFFCGIDW  HQVYIQKYTP  PLVPPRGEVN  AADAFDIGSF  489
```

FIGURE 1E

```
GRK6    N-----FKR  LGAGM-LEPP  F---KPD---  ----PQAIY--  -CKDVLDIEQ      482
GRK5    N-----FKR  LEAGM-LDPP  F---VPD---  ----PRAVY--  -CKDVLDIEQ      482
IT-11   N-----FRR  LEANM-LEPP  F---CPD---  ----PHAVY--  -CKDVLDIEQ      451
RK      S-----WRQ  LEAGM-LTPP  F---VPD---  ----SRTVY--  -AKNIQDVGA      486
GPRK2   N-----WRR  LEAGM-LEPP  F---VPD---  ----PHAVY--  -AKDVLDIEQ      323
BARK1   DEEDTKGIKL  LDSDQELYRN  FPLTISERWQ  QEVAETVFDT   INAETDRLEA      538
BARK2   DEEDTKGIKL  LDCDQDLYKN  FPLMISERWQ  QEVVETIYDA   VNAETDKIEA      538
GPRK1   DEEDTKGIKL  NDADQDLYKM  FSLTISERWQ  QEVSETVFDT   VNTETDKLEQ      539

GRK6    FSTVKGVELE  PTDQ------  ----DFYQKF  ATGSVP----   ---------I      509
GRK5    FSTVKGVNLD  HTDD------  ----DFYSKF  STGSVS----   ---------I      509
IT-11   FSAVKGIYLD  TADE------  ----DFYARF  ATGCVS----   ---------I      478
RK      FSTVKGVAFE  KADT------  ----EFFQEF  ASGTCP----   ---------I      513
GPRK2   FSTVKGVNID  ESDT------  ----NFYTKF  NTGSVS----   ---------I      350
BARK1   RKKAKNKQLG  HEEDYALGKD  CIMHGYMSKM  GNPFLTQWQR   RYFYLFPNRL      588
BARK2   RKKAKNKQLC  QEEDYAMGKD  CIMHGYMLKL  GNPFLTQWQR   RYFYLFPNRL      588
GPRK1   KRKLKQKQHF  DADE--KESD  CILHGYIKKL  GGSFASLWQT   KYAKLYPNRL      587
```

FIGURE 1F

```
GRK6    PWQNE---MVE  TE-CFQELN-  ---------  --VFGLDGSV  PPDLDWKGQP  543
GRK5    PWQNE---MIE  TE-CFKELN-  ---------  --VFGPNGTL  PPDLNRNHPP  543
IT-11   PWQNE------  -D-C---LT-  ---------  --M-VPSEK-  --EVEPKQ-C  500
RK      PWQEE---MIE  TGVFGD-LN-  ---------  ---VWRPDG-  ---QM----P  538
GPRK2   SWQNE---MME  TE-CFRELN-  ---------  --VFGPEECP  TPDLQINAAP  384
BARK1   EWRGEGEAPQ   SLLTMEEIQS  VEETQIKERK  CLLLKIRGGK  QFILQCDSDP  638
BARK2   EWRGEGESRQ   NLLTMEQIMS  VEETQIKDRK  CILLRVKGGK  QFVLQCESDP  638
GPRK1   ELHSESGNNK   PELIF--MDQ  VED--I-SSD  FILHKNENCI  QIRINDGTRD  632

GRK6    P--------- ---------  ------APP  KKGLL----Q  RLFSR-QDCC  562
GRK5    E--------- ---------  -------PP  KKGLL----Q  RLFKR-QH--  559
IT-11   ---------- ---------  ---------  ---------  ----------  -
RK      D--------- ---------  -------D-  MKGVS----G  ----------  546
GPRK2   E--------- ---------  ------PD-  KAGCF----P  --FRR-KK--  398
BARK1   ELVQWKKELR  DAYREAQQLV  QRVPKMKNKP  RSPVVELSKV  PLVQRGSA--  686
BARK2   EFAQWLKELT  CTFNEAQRLL  RRAPKFLNKP  RAAILEFSKP  PLCHRNSSGL  688
GPRK1   GRIILTNSDE  IGLKEWSSSL  RSAHKISQDL  LGSMAK-KAG  KIYGSERD--  679
```

FIGURE 1G

| | | | |
|---|---|---|---|
| GRK6 | GNCSDSEEEL PTRL----- | ------- | 576 |
| GRK5 | ---QNNSKSS PSSKTSFNHH | INSNHVSSNS TGSS--- | 590 |
| IT-11 | ---------- ---------- | ---------- ---- | - |
| RK | ---QEAAPSS KSGMCVLS-- | ---------- ---- | 561 |
| GPRK2 | ---KQPARTQ PIPIPEHLLT | THSVSSTTVE S--- | 426 |
| BARK1 | ----NGL--- ---------- | ---------- ---- | 689 |
| BARK2 | ---------- ---------- | ---------- ---- | - |
| GPRK1 | ---VNKSM-- IFGGNCSTKT | SNGSN----- ---- | 699 |

FIGURE 1H

GRK6

G PROTEIN-COUPLED RECEPTOR KINASE GRK6

This is a Rule 60 Divisional of U.S. patent application Ser. No. 08/221,817, filed Mar. 31, 1994, now U.S. Pat. No. 5,532,151, which is turn is a continuation-in-part of U.S. patent application Ser. No. 08/123,932, filed Sep. 17, 1993, now abandoned.

FIELD OF THE INVENTION

The present invention relates generally to a novel G protein-coupled receptor kinase designated GRK6 and more particularly to purified and isolated polynucleotides encoding GRK6, to methods and materials for recombinant production of GRK6 enzyme and to methods of identifying modulators of GRK6 kinase activity.

BACKGROUND

Serpentine or seven transmembrane receptors mediate signals for a wide variety of stimuli, including neurotransmitters, hormones, chemoattractants, odorants, and light [Dohlman et al., *Ann. Rev. Biochem.*, 60: 653–688 (1991); Probst et al., *DNA and Cell Biol.*, 11:1–20 (1992)]. These receptors share several common structural features, including an extracellular amino terminus, seven transmembrane spanning domains, and a cytoplasmic carboxy terminus with clustered serine and threonine residues. More than 100 members of this superfamily of receptors have been identified. These receptors are coupled to intracellular signal transduction pathways by heterotrimeric GTP-binding proteins (G proteins) [Linder et al., *Sci. Am.*, 267:56–65 (1992)].

Two G protein-coupled signal transduction mechanisms have been especially well characterized: the hormone responsive $\beta_2$-adrenergic receptor mediates catecholamine stimulation of adenyl cyclase [Dohlman et al., supra] and the light receptor rhodopsin mediates phototransduction in retinal rod cells [Khorana, *J. Biol. Chem.*, 267:1–4 (1992)]. Both receptors specifically interact with G proteins following activation by ligand. This receptor stimulation is tightly regulated such that interaction with ligand leads to a rapid and reversible loss of responsiveness of the receptor to subsequent stimulation. The process is termed homologous desensitization and is caused by phosphorylation of the receptor, usually on a cluster of serines and threonines present at the carboxy terminus [Lefkowitz, *Cell*, 74:409–412 (1993)]. Such phosphorylation is mediated by specific protein kinases which recognize the ligand-occupied receptor [Palczewski et al., *Trends Biochem. Sci.*, 16:387–391 (1991)]. The β adrenergic receptor kinase (βARK1) and rhodopsin kinase (RK) have been shown to phosphorylate the activated forms of the β-adrenergic receptor and rhodopsin, respectively. Both proteins have been purified and enzymatically characterized in reconstituted in vitro systems.

Additional lines of evidence suggest that other G protein-coupled receptors may be regulated by specific kinase, Receptor phosphorylation has been shown to be involved in desensitization in a variety of G protein-coupled systems ranging from mammalian cells [such as muscarinic cholinergic receptors, Kwatra et al., *J. Biol. Chem.*, 262:16314–16321 (1987)] to slime mold [the chemotactic cAMP receptor, Klein et al., *J. Cell Biol.*, 100:715–720 (1985)] and yeast [the mating factor α receptor, Reneke et al., *Cell*, 55:221–234 (1988)]. In addition, the carboxy terminal domain of most G protein-coupled receptors contains potential phosphorylation sites which may represent catalytic targets for such kinases.

Lorenz et al., *Proc. Natl. Acad. Sci.*, 88:8715–8719 (1991) compares the deduced amino acid sequences of human βARK1 [Benovic et al., *Science*, 246:235–240 (1989)] and bovine RK and suggests that the two molecules are structurally related. While in principle these two protein kinases could be responsible for the desensitization of the whole family of G protein-coupled receptors, recent identification of other structurally related protein kinases suggests that this is not the case. Sequences encoding three other mammalian G protein-coupled receptor kinases (GRKs) have recently been cloned, rat βARK2 [Benovic et al., *J. Biol. Chem.*, 266:14939–14946 (1991)], human IT-11 [Ambrose et al., *Hum. Mol. Genet.*, 1:697–703 (1992)] and human GRK5 [Kunapuli et al., *Proc. Natl. Acad. Sci. USA*, 90:5588–5592 (1993)], as well as sequences encoding two Drosophila GRKs (GPRK-1 and GPRK-2) [Cassill et al., *Proc. Natl. Acad. Sci. USA*, 88:11067–11070 (1991)]. The GRK family has recently been the subject of the review article Lefkowitz, supra. All of the GRKs share the highest structural homology in the centrally located catalytic domain of approximately 250 amino acids. The amino and carboxyl regions surrounding the catalytic domain are less homologous and may confer substrate specificity and subcellular localization, respectively. The GRKs are expressed in a tissue specific manner, which may further aid in the regulation of G protein-coupled signal transduction events.

G protein-coupled receptor kinases that are expressed in leukocytic cells and tissues are likely to aid the function and activities of G protein-coupled receptors expressed in these cells. Consequently, such kinases are likely to be important mediator molecules in the immune system. For example, receptors for a number of chemoattractants including fMetLeuPhe [Thomas et al., *J. Biol. Chem.*, 265:20061–20064 (1990)] and C5a [Gerard et al., *Nature*, 349:614–617 (1991)] and for the chemokines IL-8 [Holmes et al., *Science*, 253:1278–1280 (1991)], GRO [Murphy et al., *Science*, 253:1280–1283 (1991)] and MIP 1 α RANTES [Neote et al., *Cell*, 72:415–425 (1993)] have recently been identified as members of the G protein-coupled receptor superfamily. This suggests that modulation of G protein-coupled receptor kinase activity may influence health and disease states of the immune system in acute and chronic inflammation.

There thus exists a need in the an to identify G protein-coupled receptor kinases that are expressed in cells and tissues of the immune system. Elucidation of the DNA and amino acid sequences encoding such a kinase would provide information and material to allow the development of novel agents that selectively modulate the activity of the protein kinase.

SUMMARY OF THE INVENTION

The present invention provides novel purified and isolated polynucleotides (i.e., DNA and RNA, both sense and antisense strands) encoding the G protein-coupled receptor kinase designated GRK6. Preferred DNA sequences of the invention include genomic and cDNA sequences as well as wholly or partially chemically synthesized DNA sequences. The DNA sequence encoding GRK6 that is set out in SEQ ID NO: 12 and DNA sequences which hybridize to the noncoding strand thereof under stringent conditions or which would hybridize but for the redundancy of the genetic code, are contemplated by the invention. Also contemplated by the invention are biological replicas (i.e., copies of isolated DNA sequences made in vivo or in vitro) of DNA sequences of the invention. Presently preferred DNA sequences of the invention are the human GRK6 cDNA sequence set out in SEQ ID NO: 12 and the rat GRK6 cDNA sequence set out in SEQ ID NO: 21, which were respectivley deposited with the American Type Culture Collection (ATCC), 12301 Parklawn Drive, Rockville, Md. 20852, on Mar. 24, 1994 as inserts in plasmids pλ22 and pB24 which were assigned ATCC Accession Nos. 69594 and 69595. Autonomously replicating recombinant constructions such as plasmid and vital DNA vectors incorporating GRK6 sequences and especially vectors wherein DNA encoding GRK6 is operatively linked to an endogenous or exogenous expression control DNA sequence and a transcription terminator are also provided.

According to another aspect of the invention, host cells including procaryotic and eucaryotic cells, are stably transformed with DNA sequences of the invention in a manner allowing the desired GRK6 enzyme to be expressed therein. Host cells expressing GRK6 products can serve a variety of useful purposes. Such cells constitute a valuable source of immunogen for the development of antibody substances specifically immunoreactive with GRK6. Host cells of the invention are conspicuously useful in methods for the large scale production of GRK6 enzyme wherein the cells are grown in a suitable culture medium and the desired polypeptide products are isolated from the cells or from the medium in which the cells are grown by, for example, immunoaffinity purification.

GRK6 products may be obtained as isolates from natural cell sources or may be chemically synthesized, but are preferably produced by recombinant procedures involving host cells of the invention. GRK6 products having part or all of the amino acid sequence set out in SEQ ID NO: 13 are contemplated. Use of mammalian host cells is expected to provide for such post-translational modifications (e.g., myristolation, glycosylation, truncation, lipidation and tyrosine, serine or threonine phosphorylation) as may be needed to confer optimal biological activity on recombinant expression products of the invention. GRK6 products of the invention may be full length polypeptides, fragments or variants. Variants may comprise GRK6 analogs wherein one or more of the specified (i.e., naturally encoded) amino acids is deleted or replaced or wherein one or more nonspecified amino acids are added: (1). without loss of one or more of the kinase activities or immunological characteristics specific to GRK6; or (2) with specific disablement of a particular biological activity of GRK6.

Also comprehended by the present invention are antibody substances (e.g., monoclonal and polyclonal antibodies, single chain antibodies, chimetic antibodies, CDR-grafted antibodies and the like) and other binding proteins specific for GRK6. Specific binding proteins can be developed using isolated or recombinant GRK6 or GRK6 variants or cells expressing such products. Binding proteins are useful, in turn, in compositions for immunization as well as for purifying GRK6 polypeptides and detection or quantification of GRK6 enzyme in fluid and tissue samples by known immunogical procedures. They are also manifesfiy useful in modulating (i.e., blocking, inhibiting or stimulating) enzymatic activities of GRK6, especially those activities involved in signal transduction. Anti-idiotypic antibodies specific for anti-GRK6 antibody substances are also contemplated.

The scientific value of the information contributed through the disclosures of DNA and amino acid sequences of the present invention is manifest. As one series of examples, knowledge of the sequence of a cDNA for GRK6 makes possible the isolation by DNA/DNA hybridization of genomic DNA sequences encoding GRK6 and specifying GRK6 expression control regulatory sequences such as promoters, operators and the like. DNA/DNA hybridization procedures carried out with DNA sequences of the invention under stringent conditions are likewise expected to allow the isolation of DNAs encoding allelic variants of GRK6, other structurally related proteins sharing one or more of the biochemical and/or immunological properties specific to GRK6, and non-human species proteins homologous to GRK6. Polynucleotides of the invention when suitably labelled are useful in hybridization assays to detect the capacity of cells to synthesize GRK6. Polynucleotides of the invention may also be the biasis for diagnostic methods useful for identifying a genetic alteration(s) in the GRK6 locus that underlies a disease state or states. Also made available by the invention are anti-sense polynucleotides relevant to regulating expression of GRK6 by those cells which ordinarily express the same.

The DNA and amino acid sequence information provided by the present invention also makes possible the systematic analysis of the structure and function of GRK6 and definition of those molecules with which it will interact. Agents that modulate GRK6 activity may be identified by incubating a putative modulator with lysate from procaryotic or eucaryotic host cells expressing recombinant GRK6 and determining the effect of the putative modulator on GRK6 kinase activity. In a preferred embodiment the host cells lack endogenous GRK6 kinase activity. For example, *E. coli* is known to lack serine/threonine kinase activity. The selectivity of a compound that modulates the activity of GRK6 can be evaluated by comparing its activity on the GRK6 to its activity on other G protein-coupled receptor kinases. The combination of the recombinant GRK6 products of the invention with other recombinant G protein-coupled receptor kinase products in a series of independent assays provides a system for developing selective modulators of GRK6.

Selective modulators may include, for example, polypeptides or peptides which specifically bind to GRK6 or GRK6 nucleic acid, oligonucleotides which specifically bind to GRK6 or GRK6 nucleic acid and other non-peptide compounds (e.g., isolated or synthetic organic molecules) which specifically react with GRK6 or GRK6 nucleic acid. Mutant forms of GRK6 which affect the enzymatic activity or cellular localization of the wild-type protein kinase are also contemplated by the invention. Presently preferred regions of GRK6 which are targets for the development of selective modulators include, for example, the amino terminus of the enzyme (residues 1–179 of SEQ ID NO: 13) and the carboxy terminus of the enzyme (residues 452–576 of SEQ ID NO: 13). Modulators of GRK6 activity may be therapeutically useful in treatment of diseases and physiological conditions of the immune system.

BRIEF DESCRIPTION OF THE DRAWINGS

Numerous other aspects and advantages of the present invention will be apparent upon consideration of the following detailed description thereof, reference being made to the drawing wherein:

FIG. 1A to 1H is an alignment of the full length amino acid sequence of the novel human protein kinase GRK-6 with the full length sequences of previously identified protein kinases human GRK5, human IT-11, bovine RK, Drosophila GPRK-2, human βARK1, rat βARK2 and Drosophila GPRK-1.

DETAILED DESCRIPTION

Figure 2:
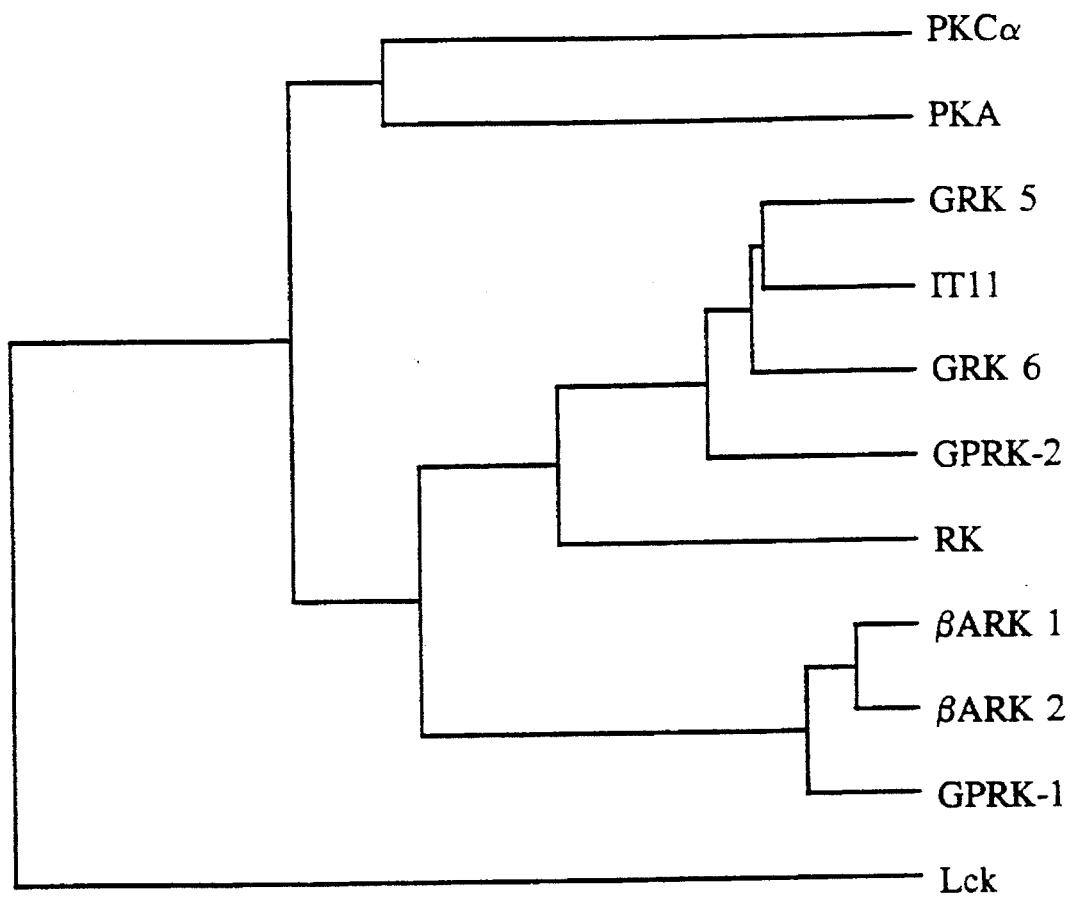
FIG. 2 is a diagram representing the evolutionary relatedness of the GRK family in comparison to two cytoplasmic serine/threonine kinases (PKC-α and PKA) and one tyrosine kinase (Lck) as determined by dendogram analysis.

The following examples illustrate the invention. Example 1 describes the isolation of a rat GRK6 cDNA fragment by PCR, the subsequent isolation of GRK6 cDNA-containing pools of human macrophage cDNAs and of a partial human GRK6 macrophage cDNA by colony hybridzation, and the isolation of a complete coding sequence for GRK6 from human placental cDNA. Example 2 characterizes the GRK6 DNA and amino acid sequences and presents a comparison of the sequences to those of previously defined GRKs. Example 3 describes the isolation of a full length rat GRK6 cDNA. Example 4 describes the construction of a vector for the bacterial expression of GRK6 and describes an assay showing that the GRK6 recombinant product has kinase activity. Example 5 relates to Northern blot assays showing the expression of GRK6 mRNA predominantly in lymphoid tissues and cell lines. Example 6 describes the down-regulation of GRK6 mRNA production in hematopoietic cell lines during differentiation. Example 7 relates to utilizing recombinant GRK6 products of the invention to develop agents that selectively modulate the enzymatic actvities of GRK6.

EXAMPLE 1

To isolate a novel GRK, degenerate oligonucleotide primers were designed for use in a PCR reaction based on sequences conserved in the catalytic domain of RK and βARK1 (Lorenz et al., supra). βARK1 and RK share significant protein homology in the putative catalytic domain (42%) which has been determined to have twelve structural subdomains [Hanks et al. Meth. *Enzymol.*, 200:38–62 (1991)]. Degenerate oligonucleotide primers were designed based on two of the most highly conserved amino acid regions present in subdomains II and VII. The sense primer designed is set out below in IUPAC nomemclature:

SEQ ID NO: 1

5' ATT<u>GGATCC</u> GCACH GGV AAR MTS TAY GCN TGY AAR 3' and encodes a BamHI site (underlined) and the amino acid sequence TGKLYA (SEQ ID NO: 2) or TGKMYA (SEQ ID NO: 3). The anti-sense primer is set out below in IUPAC nomenclature:

SEQ ID NO: 4

5'ATT<u>TCTAGA</u> DGC VAG ICC VAG RTC IGA DAT NCG NA 3! and encodes a XbaI site and the amino acid sequence VRISDLGLA (SEQ ID NO: 5).

The primers were utilized in a PCR reaction with rat T cell cDNA as template. PCR reactions consisted of about 100 ng of cDNA template, 10 µg/ml oligonucleotide primers, 50 mM KCl, 10 mM Tris HCl (pH 8.4), 1.5 mM $MgCl_2$, 200 mM dNTPs and 1 unit of Taq polymerase in a final volume of 100 µl. Reactions were heated for 7 minutes at 95° C. followed by 30 cycles of denaturation of 1 minute at 95° C., annealing for 2 minutes at 55° C. and extension for 4 minutes at 72° C. Amplified products were purified using the Magic PCR prep kit (Promega, Madison, Wis.) according to the manufacturer's instructions, digested with BamHI and XbaI, and cloned into pBluescript (SK+) (Invitrogen, San Diego, Calif.). Because the expression of βARK1 has previously been observed in leukocytic cells, PCR clones were screened by hybridization using an end-labelled oligonucleotide probe specific for βARK1:

SEQ ID NO: 6

5' TCG CTC GTC AGC ACT GGG GAC TGC CCA 3' and non-hybridizing clones were chosen for sequencing. Sequencing was performed on double stranded templates using a sequenase kit (USB, Cleveland, Ohio) according to the manufacturer's instructions. Eight non-hybridizing clones were determined to contain a PCR product of a size consistent with GRK subdomain sequences and three of eight sequences corresponded to a single novel structure with homology to other previously identified GRKs. The five other non-hybridizing sequences did not appear to encode protein kinases.

A human macrophage cDNA library was constructed by standard methods in the mammalian expression vector pRc-CMV (Invitrogen). The partial rat GRK sequence (set out in SEQ ID NO: 7) was used to design oligonucleotides for PCR amplification of a human homologue of the novel GRK from the library. The sense primer encoded a BamHI site to facilitate cloning and was:

SEQ ID NO: 8

5' ATT<u>GGATCC</u> ATG CGG ACG TGG CCG TGG TCA AG 3' The antisense primer utilized encoded a XbaI site to facilitate cloning and was:

SEQ ID NO: 9

5' ATT<u>TCTAGA</u> ATG CGG ACG TGG CCG TGG TCA AG 3' Successive rounds of PCR were performed as described above, initially to identify a pool of 100,000 positive clones and subsequenfiy to identify a sub-pool of 1000 positive clones. A single clone termed 504.3 was isolated from the sub-pool by colony hybridization using the rat PCR product labelled by random priming as a probe. The partial human macrophage cDNA clone encoded the same amino acid sequence as the cloned rat PCR fragment and was later determined to correspond to amino acids 236 to 332 of the human protein.

To isolate a full length human cDNA clone, the partial macrophage cDNA clone 504.3 was used to screen by hybridization ~1×10⁶ clones from a human placenta cDNA library made in λgt 10 by standard methods. Hybridization was performed for 16 hours at 42° C. in buffer containing 50% formamide, 5X SSC, 5X Denhardts, 0.05M Na phosphate, and 100 µg/ml salmon sperm DNA. Filters were washed in 0.2X SCC/0.1% SDS at 50° C. Five clones were subsequenfiy isolated and sub-cloned into pBluescript (SK-) (Invitrogen). Sequencing was performed using specific primers on double-stranded templates as described above. Each clone was sequenced on both strands at least once. One full length clone was identified (pλ22, ATCC 69594) and the protein encoded by its insert was named GRK6. The DNA and deduced amino acid sequences of GRK6 as originally determined are set out in SEQ ID NOs: 10 and 11. Further sequence analysis of the GRK6 insert resulted in the DNA and deduced amino acid sequences set out in SEQ ID NOs: 12 and 13, respectively. Benovic et al., *J. Biol. Chem.*, 268(26): 19521–19527 (September 1993) reports the isolation of a human heart cDNA encoding a G protein-coupled receptor kinase which was also named GRK6. The predicted amino acid sequence of the Benovic GRK6 clone differs at one position (corresponding to position 61 of SEQ ID NO: 13) from SEQ ID NO: 13 when the sequences are aligned. Haribabu et al., *Proc. Natl. Acad. Sci. USA*, 90: 9398–9402 (October 1993) describes the isolation of three G protein-coupled receptor kinase-like clones. The deduced amino acid sequence of one clone (GPRK6) lacks the thirty-three amino terminal amino acids of SEQ ID NO: 13 and differs at four positions (corresponding to positions 60, 61, 104 and 105 of SEQ ID NO: 13) from SEQ ID NO: 13 when the sequences are aligned. Adams et al., *Nature*, 355:632–634 (1992) reports the deposit of the sequence of an "expressed sequence tag" (EST 00538) in the EMBL nucleotide database. The 370-nucleotide EST corresponds to nucleotides 1 to 370 of SEQ ID NO: 12 but differs from SEQ ID NO: 12 at twelve positions when the sequences are aligned. The twelve differences include eight unidentified nucleotides in the EST and four nucleotides which are insertions or deletions made apparent by alignment of the sequences.

GRK6 is approximately 1000 bases in length (only a portion of the 3' untranslated region is presented in SEQ ID NO: 12). The overall length of the cDNA (~3000 bp) corresponds well to the observed size of hybridizing message seen on Northern blots (see Example 5). The protein sequence of GRK6 contains a centrally located protein kinase catalytic domain of 272 residues (residues 180 to 451 of SEQ ID NO: 13) which is flanked by an amino terminal domain of about 179 residues and a carboxy terminal domain of 96 residues.

A comparison of the amino acid sequence of the putative catalytic domain of GRK6 with sequences of the catalytic domains of other GRKs, the more distantly related tyrosine kinase Lck [Koga et al., *Eur. J. Immunol.*, 16:1643–1646 (1986)], and the unrelated serine/threonine kinases PKA [Maldonado et al., *Nuc. Acids Res.*, 16:8189–8190 (1988)] and PKCα [Parker et al., *Science*, 233:853–859 (1986)] was performed using the Geneworks program (Mountain View, Calif.). Results of the comparison are set out in Table 1 below as percentages of amino acid identity.

TABLE 1

|        | IT-11 | GRK5 | GPRK-2 | RK | βARK1 | βARK2 | GPRK-1 | PKA | PKCα | Lck |
|--------|-------|------|--------|-----|-------|-------|--------|-----|------|-----|
| GRK6   | 77    | 75   | 69     | 56  | 49    | 49    | 47     | 35  | 36   | 15  |
| IT-11  |       | 79   | 70     | 56  | 46    | 45    | 47     | 35  | 38   | 16  |
| GRK5   |       |      | 74     | 56  | 49    | 47    | 47     | 34  | 38   | 10  |
| GPRK-2 |       |      |        | 52  | 45    | 43    | 45     | 32  | 37   | 23  |
| RK     |       |      |        |     | 42    | 42    | 41     | 37  | 39   | 21  |
| βARK1  |       |      |        |     |       | 90    | 83     | 34  | 33   | 19  |
| βARK2  |       |      |        |     |       |       | 83     | 34  | 33   | 21  |
| GPRK-1 |       |      |        |     |       |       |        | 33  | 33   | 22  |
| PKA    |       |      |        |     |       |       |        |     | 40   | 18  |
| PKCα   |       |      |        |     |       |       |        |     |      | 25  |

The GRK6 catalytic domain is most similar to the catalytic domains of protein kinases IT-11 and GRK5.

A alignment of the full length amino acid sequence of the human GRK6 clone (SEQ ID NO: 13) and the full length amino acid sequences of human GRK5 (SEQ ID NO: 14), human IT-11 (SEQ ID NO: 15), bovine RK (SEQ ID NO: 16), Drosophila GPRK-2 (SEQ ID NO: 17), human βARK1 (SEQ ID NO: 18), rat βARK2 (SEQ ID NO: 19) and Drosophila GPRK-1 (SEQ ID NO: 20) is presented in FIG. 1A to 1H. The alignment and the phylogenetic tree depicted in FIG. 2 demonstrate that GRK5, GRK6, IT-11, and GPRK-2 form a distinct branch of the GRK family that is more similar to rhodopsin kinase than to βARK1, βARK2, and GPRK-1. The regions flanking the GRK6 catalytic domain are much less similar to other GRK sequences than the GRK6 catalytic domain itself and contain numerous insertions and deletions (for example, the Drosophila GPRK-2 has a very short amino terminal domain compared to GRK6). The function of these flanking domains is not known with certainty, but they may be involved with intracellular localization, association with the cellular membrane, interaction with G protein subunits, or confer substrate specificity. For example, RK contains a functional CAAX box at its carboxy terminus which is thought to mediate its association with the plasma membrane [Inglere et al., *J. Biol. Chem.*, 267:1422–1425 (1992)]. GRK6 lacks this sequence but does contain two potential sites for myristolation at its amino terminus which may provide a similar membrane associative function. In addition, antibodies to the amino terminus of RK block its association with rhodopsin, suggesting that this portion of the protein may be important in targeting the protein kinase to its substrate(s) [Palczewski et al., *J. Biol. Chem.*, 268:6004–6013 (1993)].

EXAMPLE 2

The open reading frame of the full length human cDNA GRK6 clone (SEQ ID NO: 12) encodes a protein of 576 amino acids, with a predicted molecular mass of 63.3 kDa. Upstream of the potential ATG initiation codon are 30 residues of 5' untranslated sequence which are typically G-C rich. The sequence surrounding this ATG is not optimal for translation initiation [Kozak, *J. Cell. Biol.*, 115:887–903 (1991)] since it contains a cysteine at the -3 position instead of an adenine or guanine. Nevertheless, this ATG is likely to be the GRK6 initiating methionine residue because (1) the other surrounding residues abide by the Kozak consensus; (2) homology comparisons with other GRKs suggest that it is the appropriate start position; and (3) GRK5 also has a similar unusual Kozak sequence with a thymine at position -3 (Kunapuli et al., supra). The 3' untranslated region of

EXAMPLE 3

A full length GRK6 clone was isolated from a rat thymus library using the original PCR fragment (see Example 1) amplified from rat T cell cDNA.

The rat PCR fragment was labelled by random priming and was initially used to screen approximately 1×10⁶ clones from a rat placental library in λgt10. Screening conditions identical to those described in Example 2 for isolation of the full length human GRK6 clone were utilized. Seven rat clones were identified, the longest of which (λ1) had a 1.4 kb insert. This clone was then used to screen an oligo dt primed cDNA library in λgt10 made from the rat T cell line BP3 [Bouwer et al., *Cellular Immunol.*, 131:219–231 (1990)]. Screening of about 1×10⁶ clones from this library yielded seven new clones, the longest of which (λ2) was not full length. The λ2 clone was then used to screen approximately 1×10⁶ clones from a second library made from BP3 that was both oligo dt and random primed. A clone obtained from this screening (λ4) extended the 5' sequence of rat GRK6 by 450 nucleotides but still lacked 5' sequences. Next, this clone was used to screen a rat spleen cDNA library in λgt10 (Clontech, Palo Alto, Calif.). Five clones were isolated from this library but were not pursued since preliminary PCR analysis indicated that they also were incomplete. The X4 clone was finally used to screen a rat thymus cDNA library in λZAP (Stratagene, La Jolla, Calif.). Screening of approximately 1×10⁶ clones from this library yielded eleven positives, one of which (clone pB24, ATCC 69595) contained the complete coding sequence of rat GRK6. The nucleotide and deduced amino acid sequences of the insert of clone B24 are set out in SEQ ID NOs: 21 and 22. The rat and human GRK6 sequences exhibit 95% identity at the amino acid level.

EXAMPLE 4

Based on its structural similarity to other members of the GRK family, GRK-6 was predicted to encode a functional protein kinase. To determine whether this was indeed the case, the putative GRK6 catalytic domain (residues 180 to 451 of SEQ ID NO: 13) was engineered for expression in *E. coli* as a fusion protein with thioredoxin in a vector similar to pRXFUS described in LeVallie et al., *Biotechnology*, 11:187–193 (1993). Specifically, human GRK6 catalytic domain coding sequences were amplified by PCR from the Bluescript placental clone described in Example 1. The sense primer utilized encoded a XbaI site (underlined) to facilitate cloning and was:

SEQ ID NO: 23

5' ATT<u>TCTAGA</u>ATTCGTTTCCTGCAGTGGAAGTGG 3' and the antisense primer utilized encoded a HindIII site to facilitate cloning and six histidine residues to facilitate purification of the fusion protein when it is expressed and was:

SEQ ID NO: 24

Figure 3:
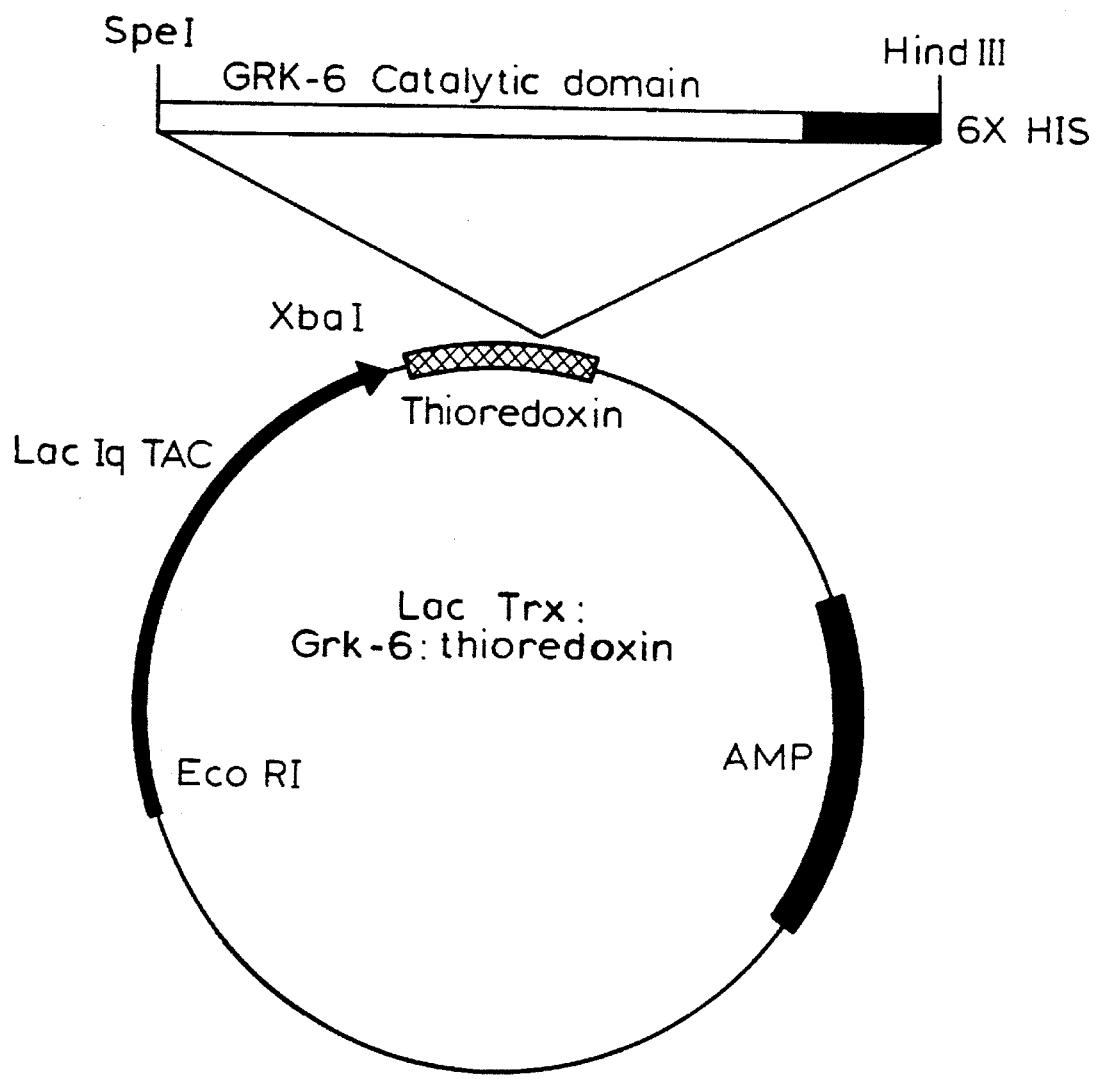
FIG. 3 is a diagram of a vector constructed for expression of GRK6 in *E. coli* as a fusion protein with thioredoxin

5' ATT<u>AAGCTT</u>TTAGTGATGGTGATGG TGATGCG-GCTCCAGCATGCCAGC 3 Digestion of the resulting PCR fragments with XbaI and HindIII allowed the fragment to be directionally cloned in frame at the carboxy terminal end of sequences encoding thioredoxin. The resulting expression vector contains the lac Iq gene, followed by the tacII promoter (from plasmid pMal-c2, New England Biolabs, Beverly, Mass.) which drives the expression of *E. coli* thioredoxin fused at the amino terminal end of the GRK6 catalytic domain. A schematic diagram of the expression vector is presented in FIG. 3.

*E. coli* XL-1 Blue cells (Stratagene, La Jolla, Calif.) were transformed with the expression vector. Transformed cells were grown at 37° C. to mid-log phase, samples were collected (to serve as controls for the induced cells) and the remaining cells induced for 2 hours with 0.4 mM IPTG at 30° C. Following induction with IPTG, soluble extracts from the clarified lysates were taken and an in vitro kinase assay was performed. Cell pellets were washed with PBS, frozen, thawed and resuspended with five times the volume of the cell pellet in kinase buffer (50 mM Tris pH 7.5, 100 mM NaCl, 12 mM $MgCl_2$ and 2.5 mM DTT) and sonicated until greater than 90% of the cells were lysed. Lysates were clarified by centrifugation and the supernatants collected. Ten μCi of $\gamma ATP^{32}$ P was added to 9 μl of clarified lysate and the reaction was incubated for 10 minutes at 30° C. The reaction was terminated by addition of 2X SDS sample buffer and the lysates resolved by SDS-PAGE. The dried gel was exposed to Hyperfilm (Amersham, Arlington Heights, Ill.) for 16 hours at −80° C. with intensifying screens.

Figure 4:
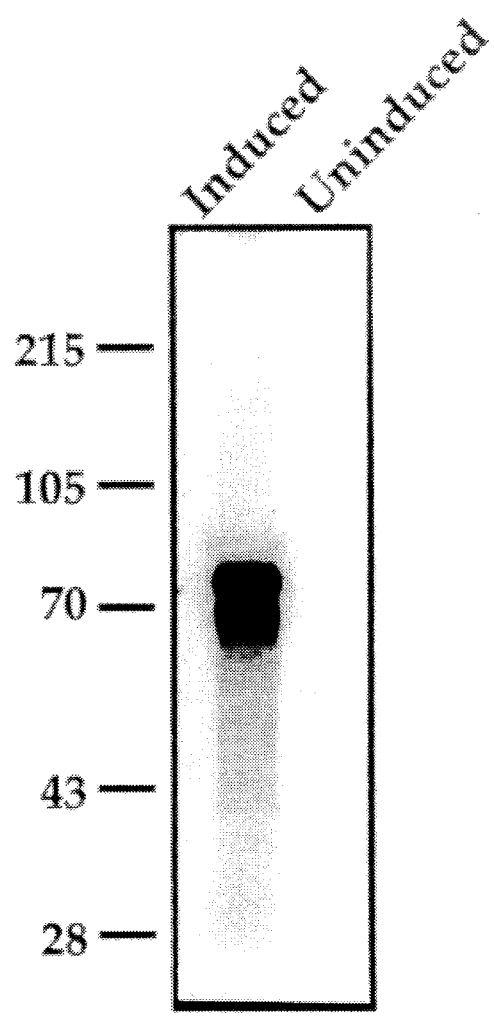
FIG. 4 is an autoradiogram showing GRK6 kinase activity in the soluble extract from *E. coli* cells in which GRK6 expression was induced but not in the soluble extract from control (uninduced) cells.

The recombinant protein including the GRK6 catalytic domain was found to phosphorylate *E. coli* proteins having a range of molecular weights (see FIG. 4) demonstrating that, in the absence of any mammalian accessory proteins, GRK6 encodes an enzymatically active protein kinase.

EXAMPLE 5

Northern blot analysis of total RNA from various human tissues indicates that GRK6 has a limited tissue distribution. Total RNA was extracted from human tissues (thymus, tonsil, brain, placenta, kidney, liver, and heart) and a number of hematopoietic cell lines (Daudi, Molt 3, H9, U937, THP-1 and HL60) using RNA Star 60 (Tel-Test B Inc., Friendswood, Tex.) according to the manufacturer's instructions. Twenty μg of total RNA was fractionated on a 1.2% formaldehyde agarose gel and blotted onto nitrocellulose. Hybridizations using a DNA probe corresponding to amino acids 265 to 513 of SEQ ID NO: 13 were performed as described in Example 1 for isolation of the full length human GRK6 clone. Blots were washed to a final stringency of 0.2X SCC and 0.1% SDS at 50° C. and were then exposed to X-ray film at −80° C. with intensifying screens for 1–6 days. The blot was stripped and reprobed with a probe specific for glyceraldehyde 3-phosphate dehydrogenase to demonstrate the integrity of the RNA.

A single GRK6 transcript of ~3kb was seen in human thymus and tonsil and at low levels in placenta, but not in human brain, heart, liver or kidney. In addition, GRK6 mRNA was detected in the human lymphoid and myeloid cell lines H9, MOLT3, Daudi, HL60, U937 and THP-1.

Figure 5:
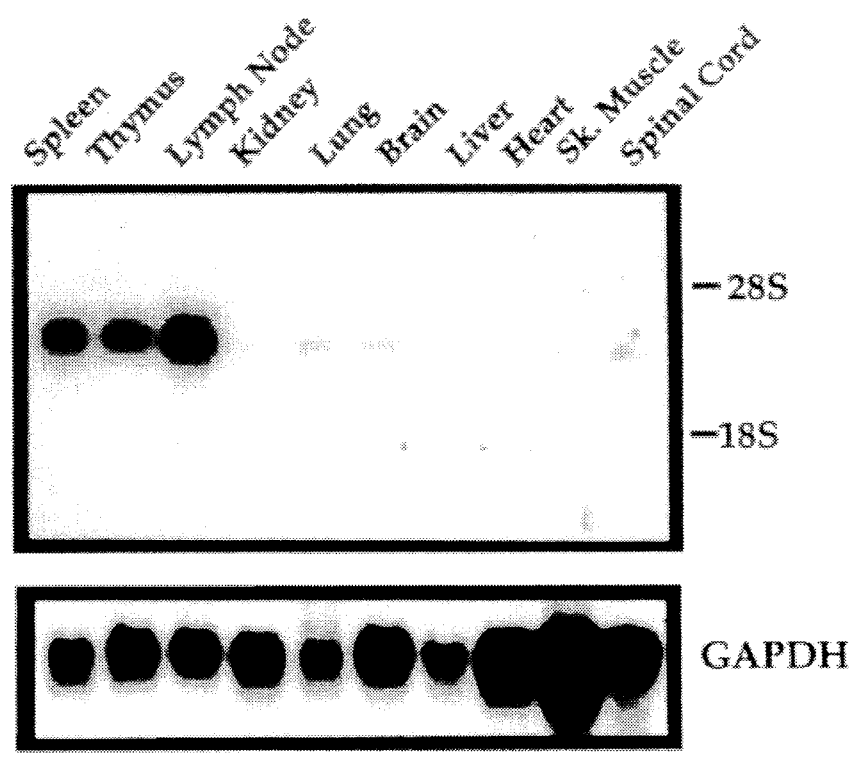
FIG. 5 is a Northern blot showing the predominant expression of GRK6 mRNA in lymphoid tissues in the rat.

Expression of GRK6 mRNA was also examined by Northern blot in rat tissues (spleen, thymus, lymph node, kidney, lung, brain, liver, heart, skeletal muscle and spinal cord). A probe corresponding to amino acids 300 to 576 of the full length rat clone (SEQ ID NO: 22) identified high levels of a single transcript of about 3 kb in spleen, thymus and lymph node. Much lower levels of expression of this transcript were also observed in non-lymphoid tissues (lung, brain, heart and spinal cord). See FIG. 5.

RK and the IT-11 gene product exhibit different, but also limited, tissue distributions. RK expression is confined to the retina and pineal gland (Lorenz et at., supra), while the IT-11 gene product (GRK4) is principally found in testis (Ambrose et al., supra). In contrast, the transcripts for GRK5, βARK1 and βARK2 show overlapping but distinctive patterns of expression in a wide range of tissues. GRK5 is expressed at the highest levels in heart, placenta and lung. It exhibits lower levels of expression in skeletal muscle, even lower levels in brain, liver and pancreas, and the lowest level of expression in kidney (Kanapuli et al., supra). βARK1 mRNA and βARK2 mRNA are found at the highest levels in nervous system tissue (e.g., cortex, hippocampus, cerebellum, brain stem and pituitary) and spleen followed by lower levels in lung, heart and kidney [Benovic et al. (1991), supra]. In most tissues βARK2 mRNA is only 10–20% of the level of βARK1 mRNA, but in the pituitary the mRNA levels are comparable.

The observation that GRKs can phosphorylate a wide range of G protein-coupled receptors in vitro raises questions concerning their substrate specificity. For example βARK1 has been shown to phosphorylate numerous receptors including the $β_2$-adrenergic receptor, the $α_2$- adrenergic receptor and the m2 muscarinic cholinergic receptors. GRK5 can phosphorylate rhodopsin, while RK can phosphorylate both rhodopsin and the $β_2$ adrenergic receptor [Kunapuli et al., supra and Benovic et al., supra]. The physiological substrates of this family of kinases may be determined at least in part by their in vivo tissue localization. The restricted expression of GRK6 suggests that it may be involved in the regulation of signaling by those serpentine receptors expressed in the immune system.

Example 6

A number of G protein-coupled receptors have been shown to be differentially expressed during hematopoiesis. For example, differentiation of the HL60 cell line along the granulocytic pathway leads to expression of the formyl peptide receptor and subsequent acquisition of responsiveness to this chemotactic peptide [Erbeck et al., *J. Immunol.*, 150:1913–1921 (1993)]. To determine whether the expression of GRK6 is regulated during differentiation, a number of hematopoietic cell lines were examined.

Figure 6:
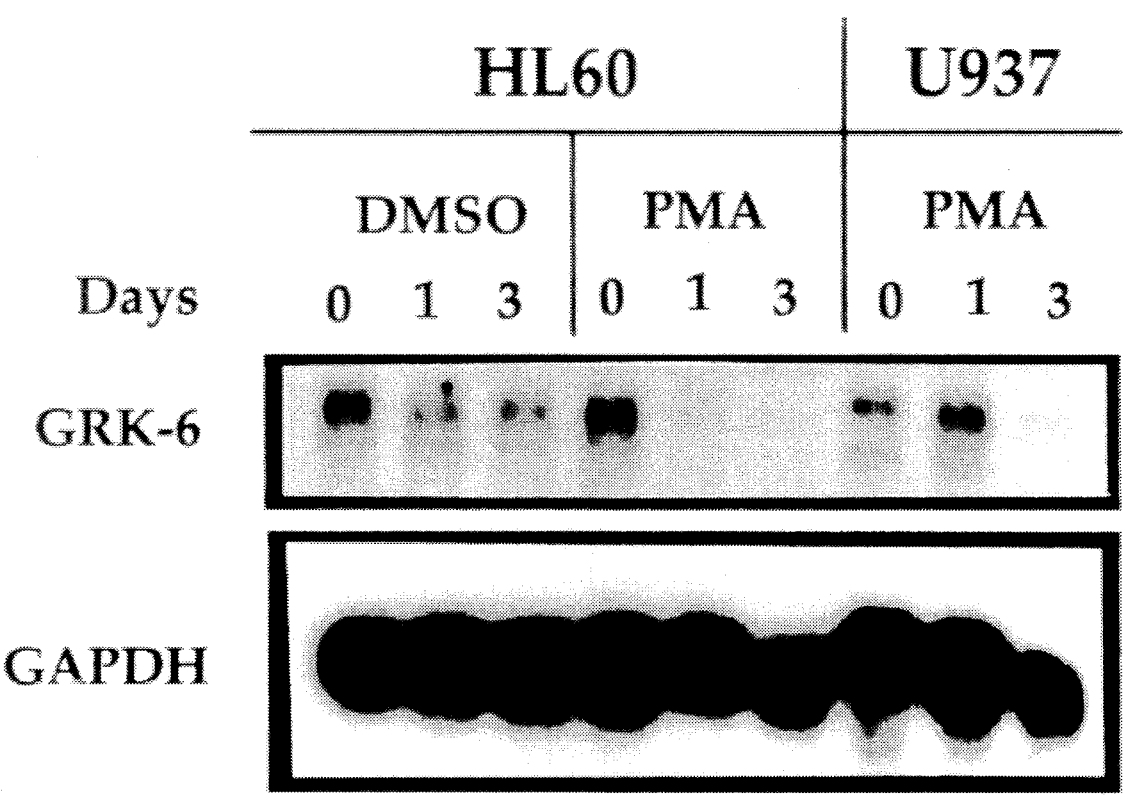
FIG. 6 is a Northern blot showing that the production of GRK6 mRNA is down-regulated during HL60 and U937 differentiation.

Differentiation of HL60 or U937 cells along the myeloid pathway by culture in the presence of 50 ng/ml phorbol ester leads to complete loss of expression of GRK6 mRNA as determined by Northern blotting of total cellular RNA (FIG. 6). In contrast, differentiation of HL-60 cells along the granulocytic pathway by culture in the presence of 1% DMSO does not appreciably change GRK6 mRNA levels. Thus down-regulation of GRK6 mRNA may be a direct response to differentiation along a particular cell lineage or may reflect a regulation of GRK6 expression by protein kinase C.

EXAMPLE 7

Developing modulators of the enzymatic activities of specific protein kinases requires differentiating the kinases present in a particular assay preparation. The classical enzymological approach of isolating protein kinases from natural tissue sources and studying each new kinase is hampered, however, by the limits of purification techniques and the inability to definitively assess whether complete resolution of a particular kinase has been achieved. One remedial approach involved identifying assay conditions which might favor the contribution of one protein kinase and minimize the contribution of others in a preparation. Still another approach has involved the separation of protein kinases by immunological means. The foregoing approaches for differentiating protein kinases are time consuming and technically difficult. As a result, many attempts to develop selective modulators of kinases have been performed with preparations containing more than one kinase. Moreover, protein kinase preparations from natural tissue sources are susceptible to limited proteolysis and may contain mixtures of active proteolytic products that have different kinetic, regulatory and physiological properties than the full length protein kinases.

Recombinant GRK6 products of the invention greatly facilitate the identification and characterization of specific GRK6 modulators. The use of human recombinant enzymes for screening for modulators has many inherent advantages. The need for purification of an protein kinase can be avoided by expressing it by recombinant methods in a host cell that has low levels or lacks endogenous GRK6 activity. Moreover, screening compounds against a recombinant human protein avoids the complicating prospect that often arises from screening against a non-human protein that a compound optimized on a non-human protein may fail to be specific for or react with the human protein. For example, a single amino acid difference between the human and rodent $5HT_{1B}$ serotonin receptors accounts for the difference in binding of a compound to the receptors. [See Oskenberg et al., *Nature*, 360:161–163 (1992)]. Once a compound that modulates the activity of GRK6 is discovered, its selectivity can be evaluated by comparing its activity on the GRK6 enzyme to its activity on other kinases. Thus, the combination of the recombinant GRK6 products of the invention with other recombinant kinase products in a series of independent assays provides a system for identifying selective modulators of GRK6. Selective modulators are expected to include, for example, (1) antibodies and other proteins or peptides which specifically bind to GRK6 or GRK6 nucleic acid, (2) oligonucleotides which specifically bind to GRK6 (see Patent Cooperation Treaty International Publication No. WO93/05182 published Mar. 18, 1993 which describes methods for selecting oligonucleotides which selectively bind to target biomolecules) or GRK6 nucleic acid (e.g., antisense oligonucleotides) and (3) other non-peptide natural or synthetic compounds which specifically bind to GRK6 or GRK6 nucleic acid. Mutant forms of GRK6 which alter the enzymatic activity of GRK6 or its localization in a cell (e.g., dominant negative mutants) are also contemplated. For example, mutation of essential residues in the catalytic domain of GRK6 (e.g., lysine 215) are predicted to generate an enzymatically non-functional kinase. If over-expressed in a cell, such a mutant GRK6 may act as a dominant negative mutant by inhibiting the wild type enzyme by competing for substrate(s). Crystallization of recombinant GRK6 alone and bound to a modulator, analysis of atomic structure by X-ray crystallography, and computer modelling of those structures are methods useful for designing and optimizing non-peptide selective modulators. See, for example, Erickson et al., *Ann. Rev. Med. Chem.*, 27:271–289 (1992) for a general review of structure-based drug design.

Regions of GRK6 that are expected to serve as targets for binding of modulators of GRK6 include, for example, the amino terminus of the enzyme (residues 1–179 of SEQ ID NO: 13), the carboxyl terminus of the enzyme (residues 452–2576 of SEQ ID NO: 13) and the central catalytic domain (residues 180–451 of SEQ ID NO: 13). Antibodies to the amino terminus of RK inhibit its interaction with rhodopsin suggesting that this region of RK meidates its interaction with substrate (Palczewski et al., supra). Because the amino and carboxy terminus are the regions of the kinases in the GRK family that are very divergent, it is likely that modulators that target within these regions of GRK6 will specifically modulate GRK6 activity and not the activity of the other members of the GRK6 family. The central catalytic domain of the GRKs, on the other hand, is relatively conserved and is essential for their activity. This region of the kinases may be used to screen for kinase inhibitors which have higher affinity for GRK6 or other kinases in the GRK family relative to other protein kinases. For example, RK is sensitive to inhibition by heparin (Palczewski et al., supra) and this sensitivity is dependent on the presence of a lysine stretch within the catalytic domain. This region is also found in other members of the GRK family including GRK6 (residues 214–225 of SEQ ID NO: 13) and agents that bind to this region of the protein kinase may preferentially inhibit protein kinases in the GRK family.

It is expected that agents which modulate the activity of GRK6 will behave as agonists or antagonists of the G protein-coupled receptor(s) which GRK6 phosphorylates.

Inhibition of βARK2 activity with specific antibodies blocks desensitisation and increases odorant induced signalling in a similar manner to a receptor agonist [Schleicher et at., *Proc. Natl. Acad. Sci. USA*, 90:1420–1424 (1993)], while overexpression of βARK1 in cell lines partially attenuates signalling through the β2 adenergic receptor in a similar manner to a receptor antagonist [Pippig et al., *J. Biol. Chem.*, 268:3201–3208 (1993)]. Thus, modulators of GRK6 activity may allow for specific regulation of G protein-coupled receptors in leucocytic cells.

While the present invention has been described in terms of specific embodiments, it is understood that variations and modifications will occur to those skilled in the art. Accordingly, only such limitations as appear in the appended claims should be placed on the invention.

We claim:

1. A purified and isolated mammalian G protien-coupled receptor kinase 6(GRK6) enzyme.

2. A purified and isolated mammalian GRK6 enzyme comprising an amino acid sequence consisting of the sequence set out in SEQ ID NO: 13.

3. A mammalian GRK6 enzyme encoded by a full length DNA sequence which hybridizes to the non-coding strand corresponding to the DNA set out in SEQ ID NO: 12 under the following conditions: hybridization at 42° C. in buffer containing 50% formamide, 5X SSC, and 0.05M Na phosphate, and washing at 50° C. in buffer containing 0.2X SSC.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
ATTGATCCGC ACHGGVAARM TSTAYGCNTG YAAR                                  3 4
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
  Thr  Gly  Lys  Leu  Tyr  Ala
  1                 5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
  Thr  Gly  Lys  Met  Tyr  Ala
  1                 5
```

( 2 ) INFORMATION FOR SEQ ID NO:4:

( i ) SEQUENCE CHARACTERISTICS:
        ( A ) LENGTH: 36 base pairs (B) TYPE: nucleic acid
(C) STRANDEDNESS: single
(D) TOPOLOGY: linear (ii) MOLECULE TYPE: DNA (ix) FEATURE:
(A) NAME/KEY: Modified-site
(B) LOCATION: group(16, 25)
(C) OTHER INFORMATION: /note="The nucleotide at each of these positions is an inosine."

(xi) SEQUENCE DESCRIPTION: SEQ ID NO:4:

ATTTCTAGAD GCVAGNCCVA GRTCNGADAT NCGNAC                36

(2) INFORMATION FOR SEQ ID NO:5:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:5:

Val Arg Ile Ser Asp Leu Gly Leu Ala
 1               5

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

TCGCTCGTCA GCACTGGGGA CTGCCCA                          27

(2) INFORMATION FOR SEQ ID NO:7:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

ATTGGATCCA TGCGGACGTG GCCGTGGTCA AG                    32

(2) INFORMATION FOR SEQ ID NO:8:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

ATTTCTAGAA TGCGGACGTG GCCGTGGTCA AG                    32

(2) INFORMATION FOR SEQ ID NO:9:

(i) SEQUENCE CHARACTERISTICS:

5,591,618

17 18

-continued ( A ) LENGTH: 294 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

| ATCCTGGAGA | AAGTGAACAG | TAGGTTTGTA | GTGAGCTTAG | CCTACGCATA | TGAGACCAAG | 60 |
| AAGCACTGT | GCCTGGTGCT | GACATTGATG | ATTGGAGGCG | ACCTCAAGTT | CCACATCTAC | 120 |
| CACATGGGCC | AGGCTGGCTT | TCCCCAAGCA | CGTGCTGTCT | ATGTCTATGC | TGCCGAGATC | 180 |
| TGCTGTGGTC | TGGAGGACTT | ACACCGGGTT | CGCATCGTGT | ACAGGGACCT | GAAGCCCGAG | 240 |
| AACATCTTGC | TGGATGACCA | CGGCCACGTC | CGCATCTCCG | ACCTTGGCCT | CGCC | 294 |

( 2 ) INFORMATION FOR SEQ ID NO:10:

( i ) SEQUENCE CHARACTERISTICS:
( A ) LENGTH: 2206 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 31..1926

( x i ) SEQUENCE DESCRIPTION: SEQ ID NO:10:

| GCCGCGGCCC GGCGGCGAGC GCGACAGCCC | ATG GAG CTC GAG AAC ATC GTA GCG | 54 |
| | Met Glu Leu Glu Asn Ile Val Ala | |
| | 1             5                 | |

| AAC ACG GTG CTA CTC AAG GCC CGG GAA GGT GGC GGT GGA AAT CGC AAA | 102 |
| Asn Thr Val Leu Leu Lys Ala Arg Glu Gly Gly Gly Gly Asn Arg Lys | |
|     10              15                  20                      | |

| GGC AAA AGC AAG AAA TGG CGG CAG ATG CTC CAG TTC CCT CAC ATC AGC | 150 |
| Gly Lys Ser Lys Lys Trp Arg Gln Met Leu Gln Phe Pro His Ile Ser | |
| 25              30                  35                      40  | |

| CAG TGC GAA GAG CTG CGG CTC AGC CTC GAG CGT GAC TAT CAC AGC CTG | 198 |
| Gln Cys Glu Glu Leu Arg Leu Ser Leu Glu Arg Asp Tyr His Ser Leu | |
|             45                  50                  55          | |

| TGC GAG CGG CAC CGC ATT GGG CGC CTG CTG TTC CGA GAG TTC TGT GCC | 246 |
| Cys Glu Arg His Arg Ile Gly Arg Leu Leu Phe Arg Glu Phe Cys Ala | |
|             60              65                  70              | |

| ACG AGG CCG GAG CTG AGC CGC TGC GTC GCC TTC CTG GAT GGG GTG GCC | 294 |
| Thr Arg Pro Glu Leu Ser Arg Cys Val Ala Phe Leu Asp Gly Val Ala | |
|         75              80                  85                  | |

| GAG TAT GAA GTG ACC CCG GAT GAC AAG CGG AAG GCA TGT GGG CGG CAC | 342 |
| Glu Tyr Glu Val Thr Pro Asp Asp Lys Arg Lys Ala Cys Gly Arg His | |
|     90              95                  100                     | |

| GTA ACG CAG AAT TTT CTG AGC CAC ACG GGT CCT GAC CTC ATC CCT GAG | 390 |
| Val Thr Gln Asn Phe Leu Ser His Thr Gly Pro Asp Leu Ile Pro Glu | |
| 105                 110                 115                 120 | |

| GTC CCC CGG CAG CTG GTG ACG GAC TGC ACC CAG CGG CTG GAG CAG GGT | 438 |
| Val Pro Arg Gln Leu Val Thr Asp Cys Thr Gln Arg Leu Glu Gln Gly | |
|             125                 130                 135         | |

| CCT GCA AAG ACC TTT TCC AGG AAC TAC CCG GCT GAC CCA CGA GTA CCT | 486 |
| Pro Ala Lys Thr Phe Ser Arg Asn Tyr Pro Ala Asp Pro Arg Val Pro | |
|             140                 145                 150         | |

| GAG CGT GGC CCC TTT GCC GAC TAC CTC GAC AGC ATC TAC TTC AAC CGT | 534 |
| Glu Arg Gly Pro Phe Ala Asp Tyr Leu Asp Ser Ile Tyr Phe Asn Arg | |
|             155                 160                 165         | |

| | | | | | | | | | | | | | | | | |
|---|---|---|---|---|---|---|---|---|---|---|---|---|---|---|---|---|
| TTC | CTG | CAG | TGG | AAG | TGG | CTG | GAA | AGG | CAG | CCA | GTG | ACC | AAA | AAC | ACC | 582 |
| Phe | Leu | Gln | Trp | Lys | Trp | Leu | Glu | Arg | Gln | Pro | Val | Thr | Lys | Asn | Thr | |
| | 170 | | | | 175 | | | | | 180 | | | | | | |
| TTC | AGG | CAA | TAC | CGA | GTC | CTG | GGT | AAA | GGT | GGC | TTT | GGG | GAG | GTG | TGC | 630 |
| Phe | Arg | Gln | Tyr | Arg | Val | Leu | Gly | Lys | Gly | Gly | Phe | Gly | Glu | Val | Cys | |
| 185 | | | | | 190 | | | | | 195 | | | | | 200 | |
| GCC | TGC | CAG | GTG | CGG | GCC | ACA | GGT | AAG | ATG | TAT | GCC | TGC | AAG | AAG | CTA | 678 |
| Ala | Cys | Gln | Val | Arg | Ala | Thr | Gly | Lys | Met | Tyr | Ala | Cys | Lys | Lys | Leu | |
| | | | | 205 | | | | | 210 | | | | | 215 | | |
| GAG | AAA | AAG | CGG | ATC | AAG | AAG | CGG | AAA | GGG | GAG | GCC | ATG | GCG | CTG | AAC | 726 |
| Glu | Lys | Lys | Arg | Ile | Lys | Lys | Arg | Lys | Gly | Glu | Ala | Met | Ala | Leu | Asn | |
| | | | 220 | | | | 225 | | | | | 230 | | | | |
| GAG | AAG | CAG | ATC | CTG | GAG | AAA | GTG | AAC | AGT | AGG | TTT | GTA | GTG | AGC | TTC | 774 |
| Glu | Lys | Gln | Ile | Leu | Glu | Lys | Val | Asn | Ser | Arg | Phe | Val | Val | Ser | Phe | |
| | | 235 | | | | 240 | | | | | 245 | | | | | |
| GGC | TAC | GCC | TAT | GAG | ACC | AAG | GAC | GCG | CTG | TGC | CTG | GTG | CTG | ACA | CTG | 822 |
| Gly | Tyr | Ala | Tyr | Glu | Thr | Lys | Asp | Ala | Leu | Cys | Leu | Val | Leu | Thr | Leu | |
| | 250 | | | | 255 | | | | | 260 | | | | | | |
| ATG | AAC | GGG | GGC | GAC | CTC | AAG | TTC | CAC | ATC | TAC | CAC | ATG | GGC | CAG | GCT | 870 |
| Met | Asn | Gly | Gly | Asp | Leu | Lys | Phe | His | Ile | Tyr | His | Met | Gly | Gln | Ala | |
| 265 | | | | | 270 | | | | | 275 | | | | | 280 | |
| GGC | TTC | CCC | GAA | GCG | CGG | GCC | GTC | TTC | TAC | GCC | GCC | GAG | ATC | TGC | TGT | 918 |
| Gly | Phe | Pro | Glu | Ala | Arg | Ala | Val | Phe | Tyr | Ala | Ala | Glu | Ile | Cys | Cys | |
| | | | | 285 | | | | | 290 | | | | | 295 | | |
| GGC | CTG | GAG | GAC | CTG | CAC | CGG | GAG | CGC | ATC | GTG | TAC | AGG | GAC | CTG | AAG | 966 |
| Gly | Leu | Glu | Asp | Leu | His | Arg | Glu | Arg | Ile | Val | Tyr | Arg | Asp | Leu | Lys | |
| | | | 300 | | | | 305 | | | | | 310 | | | | |
| CCC | GAG | AAC | ATC | TTG | CTG | GAT | GAC | CAC | GGC | CAC | ATC | CGC | ATC | TCT | GAC | 1014 |
| Pro | Glu | Asn | Ile | Leu | Leu | Asp | Asp | His | Gly | His | Ile | Arg | Ile | Ser | Asp | |
| | | 315 | | | | 320 | | | | | 325 | | | | | |
| CTG | GGA | CTA | GCT | GTG | CAT | GTG | CCC | GAG | GGC | CAG | ACC | ATC | AAA | GGG | CGT | 1062 |
| Leu | Gly | Leu | Ala | Val | His | Val | Pro | Glu | Gly | Gln | Thr | Ile | Lys | Gly | Arg | |
| | 330 | | | | 335 | | | | | 340 | | | | | | |
| GTG | GGC | ACC | GTG | GGT | TAC | ATG | GCT | CCG | GAG | GTG | GTG | AAG | AAT | GAA | CGG | 1110 |
| Val | Gly | Thr | Val | Gly | Tyr | Met | Ala | Pro | Glu | Val | Val | Lys | Asn | Glu | Arg | |
| 345 | | | | | 350 | | | | | 355 | | | | | 360 | |
| TAC | ACG | TTC | AGC | CCT | GAC | TGG | TGG | GCG | CTC | GGC | TGC | CTC | CTG | TAC | GAG | 1158 |
| Tyr | Thr | Phe | Ser | Pro | Asp | Trp | Trp | Ala | Leu | Gly | Cys | Leu | Leu | Tyr | Glu | |
| | | | | 365 | | | | | 370 | | | | | 375 | | |
| ATG | ATC | GCA | GGC | CAG | TCG | CCC | TTC | CAG | CAG | AGG | AAG | AAG | AAG | ATC | AAG | 1206 |
| Met | Ile | Ala | Gly | Gln | Ser | Pro | Phe | Gln | Gln | Arg | Lys | Lys | Lys | Ile | Lys | |
| | | | 380 | | | | 385 | | | | | 390 | | | | |
| CGG | GAG | GAG | GTG | GAG | CGG | CTG | GTG | AAG | GAG | GTC | CCC | GAG | GAG | TAT | TCC | 1254 |
| Arg | Glu | Glu | Val | Glu | Arg | Leu | Val | Lys | Glu | Val | Pro | Glu | Glu | Tyr | Ser | |
| | | 395 | | | | 400 | | | | | 405 | | | | | |
| GAG | CGC | TTT | TCC | CCG | CAG | GCC | CGC | TCA | CTT | TGC | TCA | CAG | CTC | CTC | TGC | 1302 |
| Glu | Arg | Phe | Ser | Pro | Gln | Ala | Arg | Ser | Leu | Cys | Ser | Gln | Leu | Leu | Cys | |
| | 410 | | | | 415 | | | | | 420 | | | | | | |
| AAG | GAC | CCT | GCC | GAA | CCG | ACC | CTG | GGG | TGT | CGT | GGG | GGC | AGT | GCC | CGC | 1350 |
| Lys | Asp | Pro | Ala | Glu | Pro | Thr | Leu | Gly | Cys | Arg | Gly | Gly | Ser | Ala | Arg | |
| 425 | | | | | 430 | | | | | 435 | | | | | 440 | |
| GAG | GTG | AAG | GAG | CAC | CCC | CTC | TTT | AAG | AAG | CTG | AAC | TTC | AAG | CGG | CTG | 1398 |
| Glu | Val | Lys | Glu | His | Pro | Leu | Phe | Lys | Lys | Leu | Asn | Phe | Lys | Arg | Leu | |
| | | | | 445 | | | | | 450 | | | | | 455 | | |
| GGA | GCT | GGC | ATG | CTG | GAG | CCG | CCG | TTC | AAG | CCT | GAC | CCC | CAG | GCC | ATT | 1446 |
| Gly | Ala | Gly | Met | Leu | Glu | Pro | Pro | Phe | Lys | Pro | Asp | Pro | Gln | Ala | Ile | |
| | | | 460 | | | | 465 | | | | | 470 | | | | |
| TAC | TGC | AAG | GAT | GTT | CTG | GAC | ATT | GAA | CAG | TTC | TCT | ACG | GTC | AAG | GGC | 1494 |
| Tyr | Cys | Lys | Asp | Val | Leu | Asp | Ile | Glu | Gln | Phe | Ser | Thr | Val | Lys | Gly | |
| | | 475 | | | | 480 | | | | | 485 | | | | | |

| | | | | | | | | | | | | | | | | |
|---|---|---|---|---|---|---|---|---|---|---|---|---|---|---|---|---|
| GTG | GAG | CTG | GAG | CCT | ACC | GAC | CAG | GAC | TTC | TAC | CAG | AAG | TTT | GCC | ACA | 1542 |
| Val | Glu | Leu | Glu | Pro | Thr | Asp | Gln | Asp | Phe | Tyr | Gln | Lys | Phe | Ala | Thr | |
| 490 | | | | 495 | | | | | | | 500 | | | | | |
| GGC | AGT | GTG | CCC | ATC | CCC | TGG | CAG | AAC | GAG | ATG | GTG | GAG | ACC | GAG | ATC | 1590 |
| Gly | Ser | Val | Pro | Ile | Pro | Trp | Gln | Asn | Glu | Met | Val | Glu | Thr | Glu | Ile | |
| 505 | | | | 510 | | | | | 515 | | | | | 520 | | |
| TGC | TTC | CAA | GAG | CTG | AAT | GTC | TTT | GGG | CTG | GAT | GGC | TCA | GTT | CCC | CCA | 1638 |
| Cys | Phe | Gln | Glu | Leu | Asn | Val | Phe | Gly | Leu | Asp | Gly | Ser | Val | Pro | Pro | |
| | | | | 525 | | | | | 530 | | | | | 535 | | |
| GAC | CTG | GAC | TGG | AAG | GGC | CAG | CCA | CCT | GCA | CCT | CCT | AAA | AAG | GGA | CTG | 1686 |
| Asp | Leu | Asp | Trp | Lys | Gly | Gln | Pro | Pro | Ala | Pro | Pro | Lys | Lys | Gly | Leu | |
| | | | 540 | | | | 545 | | | | | 550 | | | | |
| CTG | CAG | AGA | CTC | TTC | AGT | CGC | CAA | GAT | TGC | TGT | GGA | AAC | TGC | AGC | GAC | 1734 |
| Leu | Gln | Arg | Leu | Phe | Ser | Arg | Gln | Asp | Cys | Cys | Gly | Asn | Cys | Ser | Asp | |
| | | 555 | | | | | 560 | | | | | 565 | | | | |
| ACA | GGG | AAG | AGC | TCC | CCA | CCC | GCC | TCT | AGC | CCC | CAG | CCC | GAG | GCC | CCC | 1782 |
| Thr | Gly | Lys | Ser | Ser | Pro | Pro | Ala | Ser | Ser | Pro | Gln | Pro | Glu | Ala | Pro | |
| | 570 | | | | | 575 | | | | | 580 | | | | | |
| ACC | AGC | AGT | TGG | CGG | TAC | GAG | CTA | CTC | CGA | GCG | CCG | TTT | ACA | GTT | TTG | 1830 |
| Thr | Ser | Ser | Trp | Arg | Tyr | Glu | Leu | Leu | Arg | Ala | Pro | Phe | Thr | Val | Leu | |
| 585 | | | | | 590 | | | | | 595 | | | | | 600 | |
| CAC | AGT | GAT | CTT | CCC | CAT | TGT | CCA | CTC | AAG | TCG | TGG | CCT | GGG | GAA | CAC | 1878 |
| His | Ser | Asp | Leu | Pro | His | Cys | Pro | Leu | Lys | Ser | Trp | Pro | Gly | Glu | His | |
| | | | | 605 | | | | | 610 | | | | | 615 | | |
| AGA | CGG | AGC | TGT | CCC | CAG | TGT | CCT | CCG | TCC | CTC | AGC | CCC | TGG | CCT | GGC | 1926 |
| Arg | Arg | Ser | Cys | Pro | Gln | Cys | Pro | Pro | Ser | Leu | Ser | Pro | Trp | Pro | Gly | |
| | | | 620 | | | | 625 | | | | | 630 | | | | |

| | | | | |
|---|---|---|---|---|
| TGAGAAAGGC | AGGGCCTGGG | CCATCCCTGG | GACAAAGGTG | CGTCCCTTCA | GCTCTTCTCC | 1986 |
| GTGGAGCTCG | GGGCTTTCTG | TATTTATGTA | TTTGTACGAA | TGTATATAGC | GACCAGAGCA | 2046 |
| TTCTTAATTC | CCGCCGCAGA | CCTGGCGCCC | CCGCCTTGGC | TCCTGGGGGC | AGCCAGCCTG | 2106 |
| GCTGGAGAGC | GGGACGTGGC | AGAGGAGCCA | CTGCCAAACT | CAAGGCTCCT | CTGGCCAGCT | 2166 |
| TGGATGGCTG | AGGGTGGTCA | CACCTGAGCT | TCAGCACTGT | | | 2206 |

(2) INFORMATION FOR SEQ ID NO:11:

(i) SEQUENCE CHARACTERISTICS:
        (A) LENGTH: 632 amino acids
        (B) TYPE: amino acid
        (D) TOPOLOGY: linear (ii) MOLECULE TYPE: protein (xi) SEQUENCE DESCRIPTION: SEQ ID NO:11:

| | | | | | | | | | | | | | | |
|---|---|---|---|---|---|---|---|---|---|---|---|---|---|---|
| Met | Glu | Leu | Glu | Asn | Ile | Val | Ala | Asn | Thr | Val | Leu | Leu | Lys | Ala | Arg |
| 1 | | | | 5 | | | | | 10 | | | | | 15 | |
| Glu | Gly | Gly | Gly | Gly | Asn | Arg | Lys | Gly | Lys | Ser | Lys | Lys | Trp | Arg | Gln |
| | | | 20 | | | | | 25 | | | | | 30 | | |
| Met | Leu | Gln | Phe | Pro | His | Ile | Ser | Gln | Cys | Glu | Glu | Leu | Arg | Leu | Ser |
| | | 35 | | | | | 40 | | | | | 45 | | | |
| Leu | Glu | Arg | Asp | Tyr | His | Ser | Leu | Cys | Glu | Arg | His | Arg | Ile | Gly | Arg |
| | 50 | | | | | 55 | | | | | 60 | | | | |
| Leu | Leu | Phe | Arg | Glu | Phe | Cys | Ala | Thr | Arg | Pro | Glu | Leu | Ser | Arg | Cys |
| 65 | | | | | 70 | | | | | 75 | | | | | 80 |
| Val | Ala | Phe | Leu | Asp | Gly | Val | Ala | Glu | Tyr | Glu | Val | Thr | Pro | Asp | Asp |
| | | | | 85 | | | | | 90 | | | | | 95 | |
| Lys | Arg | Lys | Ala | Cys | Gly | Arg | His | Val | Thr | Gln | Asn | Phe | Leu | Ser | His |
| | | | 100 | | | | | 105 | | | | | 110 | | |
| Thr | Gly | Pro | Asp | Leu | Ile | Pro | Glu | Val | Pro | Arg | Gln | Leu | Val | Thr | Asp |

|     |     |     | 115 |     |     |     | 120 |     |     |     | 125 |     |     |     |
| --- | --- | --- | --- | --- | --- | --- | --- | --- | --- | --- | --- | --- | --- | --- |
| Cys | Thr | Gln | Arg | Leu | Glu | Gln | Gly | Pro | Ala | Lys | Thr | Phe | Ser | Arg | Asn |
|     | 130 |     |     |     | 135 |     |     |     |     | 140 |     |     |     |     |
| Tyr | Pro | Ala | Asp | Pro | Arg | Val | Pro | Glu | Arg | Gly | Pro | Phe | Ala | Asp | Tyr |
| 145 |     |     |     |     | 150 |     |     |     |     | 155 |     |     |     |     | 160 |
| Leu | Asp | Ser | Ile | Tyr | Phe | Asn | Arg | Phe | Leu | Gln | Trp | Lys | Trp | Leu | Glu |
|     |     |     |     | 165 |     |     |     |     | 170 |     |     |     |     | 175 |     |
| Arg | Gln | Pro | Val | Thr | Lys | Asn | Thr | Phe | Arg | Gln | Tyr | Arg | Val | Leu | Gly |
|     |     |     | 180 |     |     |     |     | 185 |     |     |     |     | 190 |     |     |
| Lys | Gly | Gly | Phe | Gly | Glu | Val | Cys | Ala | Cys | Gln | Val | Arg | Ala | Thr | Gly |
|     |     | 195 |     |     |     |     | 200 |     |     |     |     | 205 |     |     |     |
| Lys | Met | Tyr | Ala | Cys | Lys | Lys | Leu | Glu | Lys | Lys | Arg | Ile | Lys | Lys | Arg |
|     | 210 |     |     |     |     | 215 |     |     |     |     | 220 |     |     |     |     |
| Lys | Gly | Glu | Ala | Met | Ala | Leu | Asn | Glu | Lys | Gln | Ile | Leu | Glu | Lys | Val |
| 225 |     |     |     |     | 230 |     |     |     |     | 235 |     |     |     |     | 240 |
| Asn | Ser | Arg | Phe | Val | Val | Ser | Phe | Gly | Tyr | Ala | Tyr | Glu | Thr | Lys | Asp |
|     |     |     |     | 245 |     |     |     |     | 250 |     |     |     |     | 255 |     |
| Ala | Leu | Cys | Leu | Val | Leu | Thr | Leu | Met | Asn | Gly | Gly | Asp | Leu | Lys | Phe |
|     |     |     | 260 |     |     |     |     | 265 |     |     |     |     | 270 |     |     |
| His | Ile | Tyr | His | Met | Gly | Gln | Ala | Gly | Phe | Pro | Glu | Ala | Arg | Ala | Val |
|     |     | 275 |     |     |     |     | 280 |     |     |     |     | 285 |     |     |     |
| Phe | Tyr | Ala | Ala | Glu | Ile | Cys | Cys | Gly | Leu | Glu | Asp | Leu | His | Arg | Glu |
| 290 |     |     |     |     | 295 |     |     |     |     | 300 |     |     |     |     |     |
| Arg | Ile | Val | Tyr | Arg | Asp | Leu | Lys | Pro | Glu | Asn | Ile | Leu | Leu | Asp | Asp |
| 305 |     |     |     |     | 310 |     |     |     |     | 315 |     |     |     |     | 320 |
| His | Gly | His | Ile | Arg | Ile | Ser | Asp | Leu | Gly | Leu | Ala | Val | His | Val | Pro |
|     |     |     |     | 325 |     |     |     |     | 330 |     |     |     |     | 335 |     |
| Glu | Gly | Gln | Thr | Ile | Lys | Gly | Arg | Val | Gly | Thr | Val | Gly | Tyr | Met | Ala |
|     |     |     | 340 |     |     |     |     | 345 |     |     |     |     | 350 |     |     |
| Pro | Glu | Val | Val | Lys | Asn | Glu | Arg | Tyr | Thr | Phe | Ser | Pro | Asp | Trp | Trp |
|     |     | 355 |     |     |     |     | 360 |     |     |     |     | 365 |     |     |     |
| Ala | Leu | Gly | Cys | Leu | Leu | Tyr | Glu | Met | Ile | Ala | Gly | Gln | Ser | Pro | Phe |
|     | 370 |     |     |     |     | 375 |     |     |     |     | 380 |     |     |     |     |
| Gln | Gln | Arg | Lys | Lys | Lys | Ile | Lys | Arg | Glu | Glu | Val | Glu | Arg | Leu | Val |
| 385 |     |     |     |     | 390 |     |     |     |     | 395 |     |     |     |     | 400 |
| Lys | Glu | Val | Pro | Glu | Glu | Tyr | Ser | Glu | Arg | Phe | Ser | Pro | Gln | Ala | Arg |
|     |     |     |     | 405 |     |     |     |     | 410 |     |     |     |     | 415 |     |
| Ser | Leu | Cys | Ser | Gln | Leu | Leu | Cys | Lys | Asp | Pro | Ala | Glu | Pro | Thr | Leu |
|     |     |     | 420 |     |     |     |     | 425 |     |     |     |     | 430 |     |     |
| Gly | Cys | Arg | Gly | Gly | Ser | Ala | Arg | Glu | Val | Lys | Glu | His | Pro | Leu | Phe |
|     |     | 435 |     |     |     |     | 440 |     |     |     |     | 445 |     |     |     |
| Lys | Lys | Leu | Asn | Phe | Lys | Arg | Leu | Gly | Ala | Gly | Met | Leu | Glu | Pro | Pro |
|     | 450 |     |     |     |     | 455 |     |     |     |     | 460 |     |     |     |     |
| Phe | Lys | Pro | Asp | Pro | Gln | Ala | Ile | Tyr | Cys | Lys | Asp | Val | Leu | Asp | Ile |
| 465 |     |     |     |     | 470 |     |     |     |     | 475 |     |     |     |     | 480 |
| Glu | Gln | Phe | Ser | Thr | Val | Lys | Gly | Val | Glu | Leu | Glu | Pro | Thr | Asp | Gln |
|     |     |     |     | 485 |     |     |     |     | 490 |     |     |     |     | 495 |     |
| Asp | Phe | Tyr | Gln | Lys | Phe | Ala | Thr | Gly | Ser | Val | Pro | Ile | Pro | Trp | Gln |
|     |     |     | 500 |     |     |     |     | 505 |     |     |     |     | 510 |     |     |
| Asn | Glu | Met | Val | Glu | Thr | Glu | Ile | Cys | Phe | Gln | Glu | Leu | Asn | Val | Phe |
|     |     | 515 |     |     |     |     | 520 |     |     |     |     | 525 |     |     |     |
| Gly | Leu | Asp | Gly | Ser | Val | Pro | Pro | Asp | Leu | Asp | Trp | Lys | Gly | Gln | Pro |
|     | 530 |     |     |     |     | 535 |     |     |     |     | 540 |     |     |     |     |

| Pro | Ala | Pro | Pro | Lys | Lys | Gly | Leu | Leu | Gln | Arg | Leu | Phe | Ser | Arg | Gln |
| 545 | | | | 550 | | | | | 555 | | | | | | 560 |

| Asp | Cys | Cys | Gly | Asn | Cys | Ser | Asp | Thr | Gly | Lys | Ser | Ser | Pro | Pro | Ala |
| | | | | 565 | | | | | 570 | | | | | 575 | |

| Ser | Ser | Pro | Gln | Pro | Glu | Ala | Pro | Thr | Ser | Ser | Trp | Arg | Tyr | Glu | Leu |
| | | | 580 | | | | | 585 | | | | | 590 | | |

| Leu | Arg | Ala | Pro | Phe | Thr | Val | Leu | His | Ser | Asp | Leu | Pro | His | Cys | Pro |
| | | 595 | | | | | 600 | | | | | 605 | | | |

| Leu | Lys | Ser | Trp | Pro | Gly | Glu | His | Arg | Arg | Ser | Cys | Pro | Gln | Cys | Pro |
| | 610 | | | | | 615 | | | | | 620 | | | | |

| Pro | Ser | Leu | Ser | Pro | Trp | Pro | Gly |
| 625 | | | | | 630 | | |

( 2 ) INFORMATION FOR SEQ ID NO:12:

( i ) SEQUENCE CHARACTERISTICS:
( A ) LENGTH: 2204 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 31..1758

( x i ) SEQUENCE DESCRIPTION: SEQ ID NO:12:

```
GCCGCGGCCC GGCGGCGAGC GCGACAGCCC ATG GAG CTC GAG AAC ATC GTA GCG              54
                                Met Glu Leu Glu Asn Ile Val Ala
                                  1               5

AAC ACG GTG CTA CTC AAG GCC CGG GAA GGT GGC GGT GGA AAT CGC AAA              102
Asn Thr Val Leu Leu Lys Ala Arg Glu Gly Gly Gly Gly Asn Arg Lys
         10                  15                  20

GGC AAA AGC AAG AAA TGG CGG CAG ATG CTC CAG TTC CCT CAC ATC AGC              150
Gly Lys Ser Lys Lys Trp Arg Gln Met Leu Gln Phe Pro His Ile Ser
 25                  30                  35                  40

CAG TGC GAA GAG CTG CGG CTC AGC CTC GAG CGT GAC TAT CAC AGC CTG              198
Gln Cys Glu Glu Leu Arg Leu Ser Leu Glu Arg Asp Tyr His Ser Leu
                 45                  50                  55

TGC GAG CGG CAC CGC ATT GGG CGC CTG CTG TTC CGA GAG TTC TGT GCC              246
Cys Glu Arg His Arg Ile Gly Arg Leu Leu Phe Arg Glu Phe Cys Ala
                     60                  65                  70

ACG AGG CCG GAG CTG AGC CGC TGC GTC GCC TTC CTG GAT GGG GTG GCC              294
Thr Arg Pro Glu Leu Ser Arg Cys Val Ala Phe Leu Asp Gly Val Ala
             75                  80                  85

GAG TAT GAA GTG ACC CCG GAT GAC AAG CGG AAG GCA TGT GGG CGG CAC              342
Glu Tyr Glu Val Thr Pro Asp Asp Lys Arg Lys Ala Cys Gly Arg His
         90                  95                 100

GTA ACG CAG AAT TTT CTG AGC CAC ACG GGT CCT GAC CTC ATC CCT GAG              390
Val Thr Gln Asn Phe Leu Ser His Thr Gly Pro Asp Leu Ile Pro Glu
105                 110                 115                 120

GTC CCC CGG CAG CTG GTG ACG AAC TGC ACC CAG CGG CTG GAG CAG GGT              438
Val Pro Arg Gln Leu Val Thr Asn Cys Thr Gln Arg Leu Glu Gln Gly
                125                 130                 135

CCC TGC AAA GAC CTT TTC CAG GAA CTC ACC CGG CTG ACC CAC GAG TAC              486
Pro Cys Lys Asp Leu Phe Gln Glu Leu Thr Arg Leu Thr His Glu Tyr
            140                 145                 150

CTG AGC GTG GCC CCT TTT GCC GAC TAC CTC GAC AGC ATC TAC TTC AAC              534
Leu Ser Val Ala Pro Phe Ala Asp Tyr Leu Asp Ser Ile Tyr Phe Asn
        155                 160                 165

CGT TTC CTG CAG TGG AAG TGG CTG GAA AGG CAG CCA GTG ACC AAA AAC              582
```

```
Arg Phe Leu Gln Trp Lys Trp Leu Glu Arg Gln Pro Val Thr Lys Asn
170                 175                     180

ACC TTC AGG CAA TAC CGA GTC CTG GGT AAA GGT GGC TTT GGG GAG GTG                 630
Thr Phe Arg Gln Tyr Arg Val Leu Gly Lys Gly Gly Phe Gly Glu Val
185             190                 195                     200

TGC GCC TGC CAG GTG CGG GCC ACA GGT AAG ATG TAT GCC TGC AAG AAG                 678
Cys Ala Cys Gln Val Arg Ala Thr Gly Lys Met Tyr Ala Cys Lys Lys
                205                 210                     215

CTA GAG AAA AAG CGG ATC AAG AAG CGG AAA GGG GAG GCC ATG GCG CTG                 726
Leu Glu Lys Lys Arg Ile Lys Lys Arg Lys Gly Glu Ala Met Ala Leu
            220                 225                 230

AAC GAG AAG CAG ATC CTG GAG AAA GTG AAC AGT AGG TTT GTA GTG AGC                 774
Asn Glu Lys Gln Ile Leu Glu Lys Val Asn Ser Arg Phe Val Val Ser
        235                 240                 245

TTG GCC TAC GCC TAT GAG ACC AAG GAC GCG CTG TGC CTG GTG CTG ACA                 822
Leu Ala Tyr Ala Tyr Glu Thr Lys Asp Ala Leu Cys Leu Val Leu Thr
    250                 255                 260

CTG ATG AAC GGG GGC GAC CTC AAG TTC CAC ATC TAC CAC ATG GGC CAG                 870
Leu Met Asn Gly Gly Asp Leu Lys Phe His Ile Tyr His Met Gly Gln
265                 270                 275                 280

GCT GGC TTC CCC GAA GCG CGG GCC GTC TTC TAC GCC GCC GAG ATC TGC                 918
Ala Gly Phe Pro Glu Ala Arg Ala Val Phe Tyr Ala Ala Glu Ile Cys
                285                 290                 295

TGT GGC CTG GAG GAC CTG CAC CGG GAG CGC ATC GTG TAC AGG GAC CTG                 966
Cys Gly Leu Glu Asp Leu His Arg Glu Arg Ile Val Tyr Arg Asp Leu
            300                 305                 310

AAG CCC GAG AAC ATC TTG CTG GAT GAC CAC GGC CAC ATC CGC ATC TCT                1014
Lys Pro Glu Asn Ile Leu Leu Asp Asp His Gly His Ile Arg Ile Ser
        315                 320                 325

GAC CTG GGA CTA GCT GTG CAT GTG CCC GAG GGC CAG ACC ATC AAA GGG                1062
Asp Leu Gly Leu Ala Val His Val Pro Glu Gly Gln Thr Ile Lys Gly
    330                 335                 340

CGT GTG GGC ACC GTG GGT TAC ATG GCT CCG GAG GTG GTG AAG AAT GAA                1110
Arg Val Gly Thr Val Gly Tyr Met Ala Pro Glu Val Val Lys Asn Glu
345                 350                 355                 360

CGG TAC ACG TTC AGC CCT GAC TGG TGG GCG CTC GGC TGC CTC CTG TAC                1158
Arg Tyr Thr Phe Ser Pro Asp Trp Trp Ala Leu Gly Cys Leu Leu Tyr
                365                 370                 375

GAG ATG ATC GCA GGC CAG TCG CCC TTC CAG CAG AGG AAG AAG AAG ATC                1206
Glu Met Ile Ala Gly Gln Ser Pro Phe Gln Gln Arg Lys Lys Lys Ile
            380                 385                 390

AAG CGG GAG GAG GTG GAG CGG CTG GTG AAG GAG GTC CCC GAG GAG TAT                1254
Lys Arg Glu Glu Val Glu Arg Leu Val Lys Glu Val Pro Glu Glu Tyr
        395                 400                 405

TCC GAG CGC TTT TCC CCG CAG GCC CGC TCA CTT TGC TCA CAG CTC CTC                1302
Ser Glu Arg Phe Ser Pro Gln Ala Arg Ser Leu Cys Ser Gln Leu Leu
    410                 415                 420

TGC AAG GAC CCT GCC GAA CGC CTG GGG TGT CGT GGG GGC AGT GCC CGC                1350
Cys Lys Asp Pro Ala Glu Arg Leu Gly Cys Arg Gly Gly Ser Ala Arg
425                 430                 435                 440

GAG GTG AAG GAG CAC CCC CTC TTT AAG AAG CTG AAC TTC AAG CGG CTG                1398
Glu Val Lys Glu His Pro Leu Phe Lys Lys Leu Asn Phe Lys Arg Leu
                445                 450                 455

GGA GCT GGC ATG CTG GAG CCG CCG TTC AAG CCT GAC CCC CAG GCC ATT                1446
Gly Ala Gly Met Leu Glu Pro Pro Phe Lys Pro Asp Pro Gln Ala Ile
            460                 465                 470

TAC TGC AAG GAT GTT CTG GAC ATT GAA CAG TTC TCT ACG GTC AAG GGC                1494
Tyr Cys Lys Asp Val Leu Asp Ile Glu Gln Phe Ser Thr Val Lys Gly
        475                 480                 485

GTG GAG CTG GAG CCT ACC GAC CAG GAC TTC TAC CAG AAG TTT GCC ACA                1542
```

| | | | | | | | | | | | | | | |
|---|---|---|---|---|---|---|---|---|---|---|---|---|---|---|
|Val|Glu|Leu|Glu|Pro|Thr|Asp|Gln|Asp|Phe|Tyr|Gln|Lys|Phe|Ala|Thr|
| |490| | | |495| | | |500| | | | | | |

```
GGC AGT GTG CCC ATC CCC TGG CAG AAC GAG ATG GTG GAG ACC GAG TGC      1590
Gly Ser Val Pro Ile Pro Trp Gln Asn Glu Met Val Glu Thr Glu Cys
505             510             515             520

TTC CAA GAG CTG AAT GTC TTT GGG CTG GAT GGC TCA GTT CCC CCA GAC      1638
Phe Gln Glu Leu Asn Val Phe Gly Leu Asp Gly Ser Val Pro Pro Asp
                525             530             535

CTG GAC TGG AAG GGC CAG CCA CCT GCA CCT CCT AAA AAG GGA CTG CTG      1686
Leu Asp Trp Lys Gly Gln Pro Pro Ala Pro Pro Lys Lys Gly Leu Leu
            540             545             550

CAG AGA CTC TTC AGT CGC CAA GAT TGC TGT GGA AAC TGC AGC GAC AGC      1734
Gln Arg Leu Phe Ser Arg Gln Asp Cys Cys Gly Asn Cys Ser Asp Ser
        555             560             565

GAG GAA GAG CTC CCC ACC CGC CTC TAGCCCCCAG CCCGAGGCCC CCACCAGCAG     1788
Glu Glu Glu Leu Pro Thr Arg Leu
    570             575

TTGGCGGTAC GAGCTACTCC GAGCGCCGTT TACAGTTTTG CACAGTGATC TTCCCCATTG    1848

TCCACTCAAG TCGTGGCCTG GGAACACAG ACGGAGCTGT CCCCAGTGTC CTCCGTCCCT     1908

CAGCCCCTGG CCTGGCTGAG AAAGGCAGGG CCTGGGCCAT CCCTGGGACA AAGGTGCGTC    1968

CCTTCAGCTC TTCTCCGTGG AGCTCGGGGC TTTCTGTATT TATGTATTTG TACGAATGTA    2028

TATAGCGACC AGAGCATTCT TAATTCCCGC CGCAGACCTG GCGCCCCGC CTTGGCTCCT     2088

GGGGGCAGCC AGCCTGGCTG GAGAGCGGGA CGTGGCAGAG GAGCCACTGC CAAACTCAAG    2148

GCTCCTCTGG CCAGCTTGGA TGGCTGAGGG TGGTCACACC TGAGCTTCAG CACTGT        2204
```

( 2 ) INFORMATION FOR SEQ ID NO:13:

( i ) SEQUENCE CHARACTERISTICS:
        ( A ) LENGTH: 576 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Glu Leu Glu Asn Ile Val Ala Asn Thr Val Leu Leu Lys Ala Arg
1               5                   10                  15

Glu Gly Gly Gly Gly Asn Arg Lys Gly Lys Ser Lys Lys Trp Arg Gln
            20                  25                  30

Met Leu Gln Phe Pro His Ile Ser Gln Cys Glu Glu Leu Arg Leu Ser
        35                  40                  45

Leu Glu Arg Asp Tyr His Ser Leu Cys Glu Arg His Arg Ile Gly Arg
    50                  55                  60

Leu Leu Phe Arg Glu Phe Cys Ala Thr Arg Pro Glu Leu Ser Arg Cys
65                  70                  75                  80

Val Ala Phe Leu Asp Gly Val Ala Glu Tyr Glu Val Thr Pro Asp Asp
                85                  90                  95

Lys Arg Lys Ala Cys Gly Arg His Val Thr Gln Asn Phe Leu Ser His
            100                 105                 110

Thr Gly Pro Asp Leu Ile Pro Glu Val Pro Arg Gln Leu Val Thr Asn
        115                 120                 125

Cys Thr Gln Arg Leu Glu Gln Gly Pro Cys Lys Asp Leu Phe Gln Glu
    130                 135                 140

Leu Thr Arg Leu Thr His Glu Tyr Leu Ser Val Ala Pro Phe Ala Asp
145                 150                 155                 160

Tyr Leu Asp Ser Ile Tyr Phe Asn Arg Phe Leu Gln Trp Lys Trp Leu
```

-continued

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Glu | Arg | Gln | Pro<br>180 | Val | Thr | Lys | Asn | Thr<br>185 | Phe | Arg | Gln | Tyr<br>190 | Arg | Val | Leu |
| Gly | Lys | Gly<br>195 | Gly | Phe | Gly | Glu | Val<br>200 | Cys | Ala | Cys | Gln | Val<br>205 | Arg | Ala | Thr |
| Gly | Lys<br>210 | Met | Tyr | Ala | Cys<br>215 | Lys | Lys | Leu | Glu | Lys<br>220 | Lys | Arg | Ile | Lys | Lys |
| Arg<br>225 | Lys | Gly | Glu | Ala | Met<br>230 | Ala | Leu | Asn | Glu | Lys<br>235 | Gln | Ile | Leu | Glu | Lys<br>240 |
| Val | Asn | Ser | Arg | Phe<br>245 | Val | Val | Ser | Leu | Ala<br>250 | Tyr | Ala | Tyr | Glu | Thr<br>255 | Lys |
| Asp | Ala | Leu | Cys<br>260 | Leu | Val | Leu | Thr | Leu<br>265 | Met | Asn | Gly | Gly | Asp<br>270 | Leu | Lys |
| Phe | His | Ile<br>275 | Tyr | His | Met | Gly | Gln<br>280 | Ala | Gly | Phe | Pro | Glu<br>285 | Ala | Arg | Ala |
| Val | Phe<br>290 | Tyr | Ala | Ala | Glu | Ile<br>295 | Cys | Cys | Gly | Leu | Glu<br>300 | Asp | Leu | His | Arg |
| Glu<br>305 | Arg | Ile | Val | Tyr | Arg<br>310 | Asp | Leu | Lys | Pro | Glu<br>315 | Asn | Ile | Leu | Leu | Asp<br>320 |
| Asp | His | Gly | His | Ile<br>325 | Arg | Ile | Ser | Asp | Leu<br>330 | Gly | Leu | Ala | Val | His<br>335 | Val |
| Pro | Glu | Gly | Gln<br>340 | Thr | Ile | Lys | Gly | Arg<br>345 | Val | Gly | Thr | Val | Gly<br>350 | Tyr | Met |
| Ala | Pro | Glu<br>355 | Val | Val | Lys | Asn | Glu<br>360 | Arg | Tyr | Thr | Phe | Ser<br>365 | Pro | Asp | Trp |
| Trp | Ala<br>370 | Leu | Gly | Cys | Leu | Leu<br>375 | Tyr | Glu | Met | Ile | Ala<br>380 | Gly | Gln | Ser | Pro |
| Phe<br>385 | Gln | Gln | Arg | Lys | Lys<br>390 | Lys | Ile | Lys | Arg | Glu<br>395 | Glu | Val | Glu | Arg | Leu<br>400 |
| Val | Lys | Glu | Val | Pro<br>405 | Glu | Glu | Tyr | Ser | Glu<br>410 | Arg | Phe | Ser | Pro | Gln<br>415 | Ala |
| Arg | Ser | Leu | Cys<br>420 | Ser | Gln | Leu | Leu | Cys<br>425 | Lys | Asp | Pro | Ala | Glu<br>430 | Arg | Leu |
| Gly | Cys | Arg<br>435 | Gly | Gly | Ser | Ala | Arg<br>440 | Glu | Val | Lys | Glu | His<br>445 | Pro | Leu | Phe |
| Lys | Lys<br>450 | Leu | Asn | Phe | Lys | Arg<br>455 | Leu | Gly | Ala | Gly | Met<br>460 | Leu | Glu | Pro | Pro |
| Phe<br>465 | Lys | Pro | Asp | Pro | Gln<br>470 | Ala | Ile | Tyr | Cys | Lys<br>475 | Asp | Val | Leu | Asp | Ile<br>480 |
| Glu | Gln | Phe | Ser | Thr<br>485 | Val | Lys | Gly | Val | Glu<br>490 | Leu | Glu | Pro | Thr | Asp<br>495 | Gln |
| Asp | Phe | Tyr | Gln<br>500 | Lys | Phe | Ala | Thr | Gly<br>505 | Ser | Val | Pro | Ile | Pro<br>510 | Trp | Gln |
| Asn | Glu | Met<br>515 | Val | Glu | Thr | Glu | Cys<br>520 | Phe | Gln | Glu | Leu | Asn<br>525 | Val | Phe | Gly |
| Leu | Asp | Gly<br>530 | Ser | Val | Pro | Pro<br>535 | Asp | Leu | Asp | Trp | Lys<br>540 | Gly | Gln | Pro | Pro |
| Ala<br>545 | Pro | Pro | Lys | Lys | Gly<br>550 | Leu | Leu | Gln | Arg | Leu<br>555 | Phe | Ser | Arg | Gln | Asp<br>560 |
| Cys | Cys | Gly | Asn | Cys<br>565 | Ser | Asp | Ser | Glu | Glu<br>570 | Glu | Leu | Pro | Thr | Arg<br>575 | Leu |

( 2 ) INFORMATION FOR SEQ ID NO:14:

( i ) SEQUENCE CHARACTERISTICS:
    ( A ) LENGTH: 590 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

```
Met  Glu  Leu  Glu  Asn  Ile  Val  Ala  Asn  Thr  Val  Leu  Leu  Lys  Ala  Arg
 1              5                        10                       15

Glu  Gly  Gly  Gly  Gly  Lys  Arg  Lys  Gly  Lys  Ser  Lys  Lys  Trp  Lys  Glu
             20                        25                       30

Ile  Leu  Lys  Phe  Pro  His  Ile  Ser  Gln  Cys  Glu  Asp  Leu  Arg  Arg  Thr
             35                        40                       45

Ile  Asp  Arg  Asp  Tyr  Cys  Ser  Leu  Cys  Asp  Lys  Gln  Pro  Ile  Gly  Arg
        50                        55                       60

Leu  Leu  Phe  Arg  Gln  Phe  Cys  Glu  Thr  Arg  Pro  Gly  Leu  Glu  Cys  Tyr
 65                       70                       75                       80

Ile  Gln  Phe  Leu  Asp  Ser  Val  Ala  Glu  Tyr  Glu  Val  Thr  Pro  Asp  Glu
                  85                       90                       95

Lys  Leu  Gly  Glu  Lys  Gly  Lys  Glu  Ile  Met  Thr  Lys  Tyr  Leu  Thr  Pro
                 100                      105                      110

Lys  Ser  Pro  Val  Phe  Ile  Ala  Gln  Val  Gly  Gln  Asp  Leu  Val  Ser  Gln
             115                      120                      125

Thr  Glu  Glu  Lys  Leu  Leu  Gln  Lys  Pro  Cys  Lys  Glu  Leu  Phe  Ser  Ala
       130                      135                      140

Cys  Ala  Gln  Ser  Val  His  Glu  Tyr  Leu  Arg  Gly  Glu  Pro  Phe  His  Glu
145                      150                      155                      160

Tyr  Leu  Asp  Ser  Met  Phe  Phe  Asp  Arg  Phe  Leu  Gln  Trp  Lys  Trp  Leu
                 165                      170                      175

Glu  Arg  Gln  Pro  Val  Thr  Lys  Asn  Thr  Phe  Arg  Gln  Tyr  Arg  Val  Leu
             180                      185                      190

Gly  Lys  Gly  Gly  Phe  Gly  Glu  Val  Cys  Ala  Cys  Gln  Val  Arg  Ala  Thr
             195                      200                      205

Gly  Lys  Met  Tyr  Ala  Cys  Lys  Arg  Leu  Glu  Lys  Lys  Arg  Ile  Lys  Lys
       210                      215                      220

Arg  Lys  Gly  Glu  Ser  Met  Ala  Leu  Asn  Glu  Lys  Gln  Ile  Leu  Glu  Lys
225                      230                      235                      240

Val  Asn  Ser  Gln  Phe  Val  Val  Asn  Leu  Ala  Tyr  Ala  Tyr  Glu  Thr  Lys
                 245                      250                      255

Asp  Ala  Leu  Cys  Leu  Val  Leu  Thr  Ile  Met  Asn  Gly  Gly  Asp  Leu  Lys
             260                      265                      270

Phe  His  Ile  Tyr  Asn  Met  Gly  Asn  Pro  Gly  Phe  Glu  Glu  Glu  Arg  Ala
            275                      280                      285

Leu  Phe  Tyr  Ala  Ala  Glu  Ile  Leu  Cys  Gly  Leu  Glu  Asp  Leu  His  Arg
       290                      295                      300

Glu  Asn  Thr  Val  Tyr  Arg  Asp  Leu  Lys  Pro  Glu  Asn  Ile  Leu  Leu  Asp
305                      310                      315                      320

Asp  Tyr  Gly  His  Ile  Arg  Ile  Ser  Asp  Leu  Gly  Leu  Ala  Val  Lys  Ile
                 325                      330                      335

Pro  Glu  Gly  Asp  Leu  Ile  Arg  Gly  Arg  Val  Gly  Thr  Val  Gly  Tyr  Met
             340                      345                      350

Ala  Pro  Glu  Val  Leu  Asn  Asn  Gln  Arg  Tyr  Gly  Leu  Ser  Pro  Asp  Tyr
             355                      360                      365

Trp  Gly  Leu  Gly  Cys  Leu  Ile  Tyr  Glu  Met  Ile  Glu  Gly  Gln  Ser  Pro
       370                      375                      380
```

```
Phe  Arg  Gly  Arg  Lys  Glu  Lys  Val  Lys  Arg  Glu  Glu  Val  Asp  Arg  Arg
385                 390                 395                           400

Val  Leu  Glu  Thr  Glu  Glu  Val  Tyr  Ser  His  Lys  Phe  Ser  Glu  Glu  Ala
               405                      410                      415

Lys  Ser  Ile  Cys  Lys  Met  Leu  Leu  Thr  Lys  Asp  Ala  Lys  Gln  Arg  Leu
          420                      425                      430

Gly  Cys  Gln  Glu  Glu  Gly  Ala  Ala  Glu  Val  Lys  Arg  His  Pro  Phe  Phe
     435                      440                      445

Arg  Asn  Met  Asn  Phe  Lys  Arg  Leu  Glu  Ala  Gly  Met  Leu  Asp  Pro  Pro
     450                      455                 460

Phe  Val  Pro  Asp  Pro  Arg  Ala  Val  Tyr  Cys  Lys  Asp  Val  Leu  Asp  Ile
465                 470                 475                           480

Glu  Gln  Phe  Ser  Thr  Val  Lys  Gly  Val  Asn  Leu  Asp  His  Thr  Asp  Asp
               485                 490                           495

Asp  Phe  Tyr  Ser  Lys  Phe  Ser  Thr  Gly  Ser  Val  Ser  Ile  Pro  Trp  Gln
               500                 505                      510

Asn  Glu  Met  Ile  Glu  Thr  Glu  Cys  Phe  Lys  Glu  Leu  Asn  Val  Phe  Gly
          515                      520                      525

Pro  Asn  Gly  Thr  Leu  Pro  Pro  Asp  Leu  Asn  Arg  Asn  His  Pro  Pro  Glu
     530                      535                 540

Pro  Pro  Lys  Lys  Gly  Leu  Leu  Gln  Arg  Leu  Phe  Lys  Arg  Gln  His  Gln
545                 550                      555                      560

Asn  Asn  Ser  Lys  Ser  Ser  Pro  Ser  Ser  Lys  Thr  Ser  Phe  Asn  His  His
               565                      570                      575

Ile  Asn  Ser  Asn  His  Val  Ser  Ser  Asn  Ser  Thr  Gly  Ser  Ser
               580                      585                 590
```

( 2 ) INFORMATION FOR SEQ ID NO:15:

( i ) SEQUENCE CHARACTERISTICS:
        ( A ) LENGTH: 500 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Glu  Leu  Glu  Asn  Ile  Val  Ala  Asn  Ser  Leu  Leu  Leu  Lys  Ala  Arg
1                   5                   10                          15

Gln  Glu  Lys  Asp  Tyr  Ser  Ser  Leu  Cys  Asp  Lys  Gln  Pro  Ile  Gly  Arg
               20                  25                      30

Arg  Leu  Phe  Arg  Gln  Phe  Cys  Asp  Thr  Lys  Pro  Thr  Leu  Lys  Arg  His
          35                  40                  45

Ile  Glu  Phe  Leu  Asp  Ala  Val  Ala  Glu  Tyr  Glu  Val  Ala  Asp  Asp  Glu
     50                  55                  60

Asp  Arg  Ser  Asp  Cys  Gly  Leu  Ser  Ile  Leu  Asp  Arg  Phe  Phe  Asn  Asp
65                  70                  75                          80

Lys  Leu  Ala  Ala  Pro  Leu  Pro  Glu  Ile  Pro  Pro  Asp  Val  Val  Thr  Glu
               85                  90                      95

Cys  Arg  Leu  Gly  Leu  Lys  Glu  Glu  Asn  Pro  Ser  Lys  Lys  Ala  Phe  Glu
               100                 105                     110

Glu  Cys  Thr  Arg  Val  Ala  His  Asn  Tyr  Leu  Arg  Gly  Glu  Pro  Phe  Glu
          115                 120                     125

Glu  Tyr  Gln  Glu  Ser  Ser  Tyr  Phe  Ser  Gln  Phe  Leu  Gln  Trp  Lys  Trp
     130                     135                     140

Leu  Glu  Arg  Gln  Pro  Val  Thr  Lys  Asn  Thr  Phe  Arg  His  Tyr  Arg  Val
```

|     |     |     |     |     |     |     |     |     |     |     |     |     |     |     |     |
|---|---|---|---|---|---|---|---|---|---|---|---|---|---|---|---|
| 145 |     |     |     | 150 |     |     |     | 155 |     |     |     | 160 |     |     |     |
| Leu | Gly | Lys | Gly | Gly | Phe | Gly | Glu | Val | Cys | Ala | Cys | Gln | Val | Arg | Ala |
|     |     |     | 165 |     |     |     | 170 |     |     |     | 175 |     |     |     |     |
| Thr | Gly | Lys | Met | Tyr | Ala | Cys | Lys | Lys | Leu | Gln | Lys | Lys | Arg | Ile | Lys |
|     |     |     | 180 |     |     |     | 185 |     |     |     | 190 |     |     |     |     |
| Lys | Arg | Lys | Gly | Glu | Ala | Met | Ala | Leu | Asn | Glu | Lys | Arg | Ile | Leu | Glu |
|     |     | 195 |     |     |     | 200 |     |     |     |     | 205 |     |     |     |     |
| Lys | Val | Gln | Ser | Arg | Phe | Val | Val | Ser | Leu | Ala | Tyr | Ala | Tyr | Glu | Thr |
|     | 210 |     |     |     | 215 |     |     |     |     | 220 |     |     |     |     |     |
| Lys | Asp | Ala | Leu | Cys | Leu | Val | Leu | Thr | Ile | Met | Asn | Gly | Gly | Asp | Leu |
| 225 |     |     |     | 230 |     |     |     | 235 |     |     |     |     |     | 240 |     |
| Lys | Phe | His | Ile | Tyr | Asn | Leu | Gly | Asn | Pro | Gly | Phe | Asp | Glu | Gln | Arg |
|     |     |     | 245 |     |     |     | 250 |     |     |     | 255 |     |     |     |     |
| Ala | Val | Phe | Tyr | Ala | Ala | Glu | Leu | Cys | Cys | Gly | Leu | Glu | Asp | Leu | Gln |
|     |     | 260 |     |     |     | 265 |     |     |     |     | 270 |     |     |     |     |
| Arg | Glu | Arg | Ile | Val | Tyr | Arg | Asp | Leu | Lys | Pro | Glu | Asn | Ile | Leu | Leu |
|     | 275 |     |     |     | 280 |     |     |     |     | 285 |     |     |     |     |     |
| Asp | Asp | Arg | Gly | His | Ile | Arg | Ile | Ser | Asp | Leu | Gly | Leu | Ala | Thr | Glu |
|     | 290 |     |     |     | 295 |     |     |     |     | 300 |     |     |     |     |     |
| Ile | Pro | Glu | Gly | Gln | Arg | Val | Arg | Gly | Arg | Val | Gly | Thr | Val | Gly | Tyr |
| 305 |     |     |     | 310 |     |     |     | 315 |     |     |     |     |     | 320 |     |
| Met | Ala | Pro | Glu | Val | Val | Asn | Asn | Glu | Lys | Tyr | Thr | Phe | Ser | Pro | Asp |
|     |     |     | 325 |     |     |     | 330 |     |     |     | 335 |     |     |     |     |
| Trp | Trp | Gly | Leu | Gly | Cys | Leu | Ile | Tyr | Glu | Met | Ile | Gln | Gly | His | Ser |
|     |     | 340 |     |     |     | 345 |     |     |     |     | 350 |     |     |     |     |
| Pro | Phe | Lys | Lys | Tyr | Lys | Glu | Lys | Val | Lys | Trp | Glu | Glu | Val | Asp | Gln |
|     |     | 355 |     |     |     | 360 |     |     |     |     | 365 |     |     |     |     |
| Arg | Ile | Lys | Asn | Asp | Thr | Glu | Glu | Tyr | Ser | Glu | Lys | Phe | Ser | Glu | Asp |
|     | 370 |     |     |     | 375 |     |     |     |     | 380 |     |     |     |     |     |
| Ala | Lys | Ser | Ile | Cys | Arg | Met | Leu | Leu | Thr | Lys | Asn | Pro | Ser | Lys | Arg |
| 385 |     |     |     | 390 |     |     |     | 395 |     |     |     |     |     | 400 |     |
| Leu | Gly | Cys | Arg | Gly | Glu | Gly | Ala | Ala | Gly | Val | Lys | Gln | His | Pro | Val |
|     |     |     | 405 |     |     |     | 410 |     |     |     | 415 |     |     |     |     |
| Phe | Lys | Asp | Ile | Asn | Phe | Arg | Arg | Leu | Glu | Ala | Asn | Met | Leu | Glu | Pro |
|     |     |     | 420 |     |     |     | 425 |     |     |     | 430 |     |     |     |     |
| Pro | Phe | Cys | Pro | Asp | Pro | His | Ala | Val | Tyr | Cys | Lys | Asp | Val | Leu | Asp |
|     |     | 435 |     |     |     | 440 |     |     |     |     | 445 |     |     |     |     |
| Ile | Glu | Gln | Phe | Ser | Ala | Val | Lys | Gly | Ile | Tyr | Leu | Asp | Thr | Ala | Asp |
|     | 450 |     |     |     | 455 |     |     |     |     | 460 |     |     |     |     |     |
| Glu | Asp | Phe | Tyr | Ala | Arg | Phe | Ala | Thr | Gly | Cys | Val | Ser | Ile | Pro | Trp |
| 465 |     |     |     | 470 |     |     |     | 475 |     |     |     |     |     | 480 |     |
| Gln | Asn | Glu | Asp | Cys | Leu | Thr | Met | Val | Pro | Ser | Glu | Lys | Glu | Val | Glu |
|     |     |     | 485 |     |     |     | 490 |     |     |     | 495 |     |     |     |     |
| Pro | Lys | Gln | Cys |     |     |     |     |     |     |     |     |     |     |     |     |
|     |     |     | 500 |     |     |     |     |     |     |     |     |     |     |     |     |

( 2 ) INFORMATION FOR SEQ ID NO:16:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Met | Asp | Phe | Gly | Ser | Leu | Glu | Thr | Val | Val | Ala | Asn | Ser | Ala | Phe | Ile |
| --- | --- | --- | --- | --- | --- | --- | --- | --- | --- | --- | --- | --- | --- | --- | --- |
| 1 | | | | 5 | | | | | 10 | | | | | 15 | |
| Ala | Ala | Arg | Gly | Ser | Phe | Asp | Ala | Ser | Ser | Gly | Pro | Ala | Ser | Arg | Asp |
| | | | 20 | | | | | 25 | | | | | 30 | | |
| Arg | Lys | Tyr | Leu | Ala | Arg | Leu | Lys | Leu | Pro | Pro | Leu | Ser | Lys | Cys | Glu |
| | | | 35 | | | | 40 | | | | | 45 | | | |
| Ala | Leu | Arg | Glu | Ser | Leu | Asp | Leu | Gly | Phe | Glu | Gly | Met | Cys | Leu | Glu |
| | | | 50 | | | | | 55 | | | | | 60 | | |
| Gln | Pro | Ile | Gly | Lys | Arg | Leu | Phe | Gln | Gln | Phe | Leu | Arg | Thr | His | Glu |
| 65 | | | | | 70 | | | | | 75 | | | | | 80 |
| Gln | His | Gly | Pro | Ala | Leu | Gln | Leu | Trp | Lys | Asp | Ile | Glu | Asp | Tyr | Asp |
| | | | | 85 | | | | | 90 | | | | | 95 | |
| Thr | Ala | Asp | Asp | Ala | Leu | Arg | Pro | Gln | Lys | Ala | Gln | Ala | Leu | Arg | Ala |
| | | | 100 | | | | | 105 | | | | | 110 | | |
| Ala | Tyr | Leu | Glu | Pro | Gln | Ala | Gln | Leu | Phe | Cys | Ser | Phe | Leu | Asp | Ala |
| | | 115 | | | | | 120 | | | | | 125 | | | |
| Glu | Thr | Val | Ala | Arg | Ala | Arg | Ala | Gly | Ala | Gly | Asp | Gly | Leu | Phe | Gln |
| | 130 | | | | | 135 | | | | | 140 | | | | |
| Pro | Leu | Leu | Arg | Ala | Val | Leu | Ala | His | Leu | Gly | Gln | Ala | Pro | Phe | Gln |
| 145 | | | | | 150 | | | | | 155 | | | | | 160 |
| Glu | Phe | Leu | Asp | Ser | Leu | Tyr | Phe | Leu | Arg | Phe | Leu | Gln | Trp | Lys | Trp |
| | | | | 165 | | | | | 170 | | | | | 175 | |
| Leu | Glu | Ala | Gln | Pro | Met | Gly | Glu | Asp | Trp | Phe | Leu | Asp | Phe | Arg | Val |
| | | | | 180 | | | | | 185 | | | | | 190 | |
| Leu | Gly | Arg | Gly | Gly | Phe | Gly | Glu | Val | Phe | Ala | Cys | Gln | Met | Lys | Ala |
| | | | 195 | | | | | 200 | | | | | 205 | | |
| Thr | Gly | Lys | Leu | Tyr | Ala | Cys | Lys | Lys | Leu | Asn | Lys | Lys | Arg | Leu | Lys |
| | 210 | | | | | 215 | | | | | 220 | | | | |
| Lys | Arg | Lys | Gly | Tyr | Gln | Gly | Ala | Met | Val | Glu | Lys | Lys | Ile | Leu | Ala |
| 225 | | | | | 230 | | | | | 235 | | | | | 240 |
| Lys | Val | His | Ser | Arg | Phe | Ile | Val | Ser | Leu | Ala | Tyr | Ala | Phe | Glu | Thr |
| | | | | 245 | | | | | 250 | | | | | 255 | |
| Lys | Thr | Asp | Leu | Cys | Leu | Val | Met | Thr | Ile | Met | Asn | Gly | Gly | Asp | Ile |
| | | | 260 | | | | | 265 | | | | | 270 | | |
| Arg | Tyr | His | Ile | Tyr | Asn | Val | Asp | Glu | Asp | Asn | Pro | Gly | Phe | Gln | Glu |
| | | 275 | | | | | 280 | | | | | 285 | | | |
| Pro | Arg | Ala | Ile | Phe | Tyr | Thr | Ala | Gln | Ile | Val | Ser | Gly | Leu | Glu | His |
| | 290 | | | | | 295 | | | | | 300 | | | | |
| Leu | His | Gln | Arg | Asn | Ile | Ile | Tyr | Arg | Asp | Leu | Lys | Pro | Glu | Asn | Val |
| 305 | | | | | 310 | | | | | 315 | | | | | 320 |
| Leu | Leu | Asp | Asp | Asp | Gly | Asn | Val | Arg | Ile | Ser | Asp | Leu | Gly | Leu | Ala |
| | | | | 325 | | | | | 330 | | | | | 335 | |
| Val | Glu | Leu | Lys | Ala | Gly | Gln | Thr | Lys | Thr | Lys | Gly | Tyr | Ala | Gly | Thr |
| | | | 340 | | | | | 345 | | | | | 350 | | |
| Pro | Gly | Phe | Met | Ala | Pro | Glu | Leu | Leu | Leu | Gly | Glu | Glu | Tyr | Asp | Phe |
| | | 355 | | | | | 360 | | | | | 365 | | | |
| Ser | Val | Asp | Tyr | Phe | Ala | Leu | Gly | Val | Thr | Leu | Tyr | Glu | Met | Ile | Ala |
| | 370 | | | | | 375 | | | | | 380 | | | | |
| Ala | Arg | Gly | Pro | Phe | Arg | Ala | Arg | Gly | Glu | Lys | Val | Glu | Asn | Lys | Glu |
| 385 | | | | | 390 | | | | | 395 | | | | | 400 |
| Leu | Lys | Gln | Arg | Val | Leu | Glu | Gln | Ala | Val | Thr | Tyr | Pro | Asp | Lys | Phe |
| | | | | 405 | | | | | 410 | | | | | 415 | |
| Ser | Pro | Ala | Ser | Lys | Asp | Phe | Cys | Glu | Ala | Leu | Leu | Gln | Lys | Asp | Pro |
| | | | 420 | | | | | 425 | | | | | 430 | | |

```
Glu  Lys  Arg  Leu  Gly  Phe  Arg  Asp  Gly  Ser  Cys  Asp  Gly  Leu  Arg  Thr
     435                 440                      445

His  Pro  Leu  Phe  Arg  Asp  Ile  Ser  Trp  Arg  Gln  Leu  Glu  Ala  Gly  Met
     450                 455                      460

Leu  Thr  Pro  Pro  Phe  Val  Pro  Asp  Ser  Arg  Thr  Val  Tyr  Ala  Lys  Asn
465                      470                      475                      480

Ile  Gln  Asp  Val  Gly  Ala  Phe  Ser  Thr  Val  Lys  Gly  Val  Ala  Phe  Glu
                    485                      490                      495

Lys  Ala  Asp  Thr  Glu  Phe  Phe  Gln  Glu  Phe  Ala  Ser  Gly  Thr  Cys  Pro
                    500                 505                      510

Ile  Pro  Trp  Gln  Glu  Glu  Met  Ile  Glu  Thr  Gly  Val  Phe  Gly  Asp  Leu
          515                      520                      525

Asn  Val  Trp  Arg  Pro  Asp  Gly  Gln  Met  Pro  Asp  Asp  Met  Lys  Gly  Val
     530                      535                      540

Ser  Gly  Gln  Glu  Ala  Ala  Pro  Ser  Ser  Lys  Ser  Gly  Met  Cys  Val  Leu
545                      550                      555                      560

Ser
```

( 2 ) INFORMATION FOR SEQ ID NO:17:

( i ) SEQUENCE CHARACTERISTICS:
        ( A ) LENGTH: 426 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Tyr  Phe  His  Arg  Tyr  Leu  Gln  Trp  Lys  Trp  Leu  Glu  Ala  Gln  Pro
1                   5                   10                       15

Ile  Thr  Tyr  Lys  Thr  Phe  Arg  Met  Tyr  Arg  Val  Leu  Gly  Lys  Gly  Gly
               20                  25                       30

Phe  Gly  Glu  Val  Cys  Ala  Cys  Gln  Val  Arg  Ala  Thr  Gly  Lys  Met  Tyr
          35                       40                  45

Ala  Cys  Lys  Lys  Leu  Glu  Lys  Lys  Arg  Ile  Lys  Lys  Arg  Lys  Gly  Glu
     50                       55                       60

Ser  Met  Val  Leu  Ile  Glu  Lys  Gln  Ile  Leu  Gln  Lys  Ile  Asn  Ser  Pro
65                       70                       75                       80

Phe  Val  Val  Asn  Leu  Ala  Tyr  Ala  Tyr  Glu  Thr  Lys  Asp  Ala  Leu  Cys
                    85                       90                       95

Leu  Val  Leu  Thr  Ile  Met  Asn  Gly  Gly  Asp  Leu  Lys  Phe  His  Ile  Tyr
                    100                      105                      110

Asn  Met  Gly  Gly  Glu  Pro  Gly  Phe  Glu  Leu  Glu  Arg  Ala  Arg  Phe  Tyr
          115                      120                      125

Ala  Ala  Glu  Val  Ala  Cys  Gly  Leu  Gln  His  Leu  His  Lys  Gln  Gly  Ile
     130                      135                      140

Val  Tyr  Arg  Asp  Cys  Lys  Pro  Glu  Asn  Ile  Leu  Leu  Asp  Asp  His  Gly
145                      150                      155                      160

His  Val  Arg  Ile  Ser  Asp  Leu  Gly  Leu  Ala  Val  Glu  Ile  Pro  Glu  Gly
               165                      170                      175

Glu  Met  Val  Arg  Gly  Arg  Val  Gly  Thr  Val  Gly  Tyr  Met  Ala  Pro  Glu
          180                      185                      190

Val  Ile  Asp  Asn  Glu  Lys  Tyr  Ala  Phe  Ser  Pro  Asp  Trp  Phe  Ser  Phe
          195                      200                      205

Gly  Cys  Leu  Leu  Tyr  Glu  Met  Ile  Glu  Gly  Gln  Ala  Pro  Phe  Arg  Met
     210                      215                      220
```

| Arg<br>225 | Lys | Glu | Lys | Val | Lys<br>230 | Arg | Glu | Glu | Val | Asp<br>235 | Arg | Arg | Val | Lys | Glu<br>240 |
|---|---|---|---|---|---|---|---|---|---|---|---|---|---|---|---|
| Asp | Pro | Glu | Lys | Tyr<br>245 | Ser | Ser | Lys | Phe | Asn<br>250 | Asp | Glu | Ala | Lys | Ser<br>255 | Met |
| Cys | Gln | Gln | Leu<br>260 | Leu | Ala | Lys | Ser | Ile<br>265 | Lys | Gln | Arg | Leu | Gly<br>270 | Cys | Arg |
| Asn | Gly | Arg<br>275 | Met | Gly | Gly | Gln | Asp<br>280 | Val | Met | Ala | His | Pro<br>285 | Phe | Phe | His |
| Ser | Thr<br>290 | Gln | Leu | Asn | Trp | Arg<br>295 | Arg | Leu | Glu | Ala | Gly<br>300 | Met | Leu | Glu | Pro |
| Pro<br>305 | Phe | Val | Pro | Asp | Pro<br>310 | His | Ala | Val | Tyr | Ala<br>315 | Lys | Asp | Val | Leu | Asp<br>320 |
| Ile | Glu | Gln | Phe | Ser<br>325 | Thr | Val | Lys | Gly | Val<br>330 | Asn | Ile | Asp | Glu | Ser<br>335 | Asp |
| Thr | Asn | Phe | Tyr<br>340 | Thr | Lys | Phe | Asn | Thr<br>345 | Gly | Ser | Val | Ser | Ile<br>350 | Ser | Trp |
| Gln | Asn | Glu<br>355 | Met | Met | Glu | Thr | Glu<br>360 | Cys | Phe | Arg | Glu | Leu<br>365 | Asn | Val | Phe |
| Gly | Pro<br>370 | Glu | Glu | Cys | Pro | Thr<br>375 | Pro | Asp | Leu | Gln | Ile<br>380 | Asn | Ala | Ala | Pro |
| Glu<br>385 | Pro | Asp | Lys | Ala | Gly<br>390 | Cys | Phe | Pro | Phe | Arg<br>395 | Arg | Lys | Lys | Lys | Gln<br>400 |
| Pro | Ala | Arg | Thr | Gln<br>405 | Pro | Ile | Pro | Ile | Pro<br>410 | Glu | His | Leu | Leu | Thr<br>415 | Thr |
| His | Ser | Val | Ser<br>420 | Ser | Thr | Thr | Val | Glu<br>425 | Ser |  |  |  |  |  |  |

( 2 ) INFORMATION FOR SEQ ID NO:18:

( i ) SEQUENCE CHARACTERISTICS:
        ( A ) LENGTH: 689 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Met<br>1 | Ala | Asp | Leu | Glu<br>5 | Ala | Val | Leu | Ala | Asp<br>10 | Val | Ser | Tyr | Leu | Met<br>15 | Ala |
|---|---|---|---|---|---|---|---|---|---|---|---|---|---|---|---|
| Met | Glu | Lys | Ser<br>20 | Lys | Ala | Thr | Pro | Ala<br>25 | Ala | Arg | Ala | Ser | Lys<br>30 | Lys | Ile |
| Leu | Leu | Pro<br>35 | Glu | Pro | Ser | Ile | Arg<br>40 | Ser | Val | Met | Gln | Lys<br>45 | Tyr | Leu | Glu |
| Asp | Arg<br>50 | Gly | Glu | Val | Thr | Phe<br>55 | Glu | Lys | Ile | Phe | Ser<br>60 | Gln | Lys | Leu | Gly |
| Tyr<br>65 | Leu | Leu | Phe | Arg | Asp<br>70 | Phe | Cys | Leu | Asn | His<br>75 | Leu | Glu | Glu | Ala | Arg<br>80 |
| Pro | Leu | Val | Glu | Phe<br>85 | Tyr | Glu | Glu | Ile | Lys<br>90 | Lys | Tyr | Glu | Lys | Leu<br>95 | Glu |
| Thr | Glu | Glu | Glu<br>100 | Arg | Val | Ala | Arg | Ser<br>105 | Arg | Glu | Ile | Phe | Asp<br>110 | Ser | Tyr |
| Ile | Met | Lys<br>115 | Glu | Leu | Leu | Ala | Cys<br>120 | Ser | His | Pro | Phe | Ser<br>125 | Lys | Ser | Ala |
| Thr | Glu<br>130 | His | Val | Gln | Gly | His<br>135 | Leu | Gly | Lys | Lys | Gln<br>140 | Val | Pro | Pro | Asp |
| Leu | Phe | Gln | Pro | Tyr | Ile | Glu | Glu | Ile | Cys | Gln | Asn | Leu | Arg | Gly | Asp |

-continued

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Val | Phe | Gln | Lys | Phe | Ile | Glu | Ser | Asp | Lys | Phe | Thr | Arg | Phe | Cys | Gln |
|     |     |     |     | 165 |     |     |     |     | 170 |     |     |     |     | 175 |     |
| Trp | Lys | Asn | Val | Glu | Leu | Asn | Ile | His | Leu | Thr | Met | Asn | Asp | Phe | Ser |
|     |     |     | 180 |     |     |     |     | 185 |     |     |     |     | 190 |     |     |
| Val | His | Arg | Ile | Ile | Gly | Arg | Gly | Gly | Phe | Gly | Glu | Val | Tyr | Gly | Cys |
|     |     | 195 |     |     |     |     | 200 |     |     |     |     | 205 |     |     |     |
| Arg | Lys | Ala | Asp | Thr | Gly | Lys | Met | Tyr | Ala | Met | Lys | Cys | Leu | Asp | Lys |
|     | 210 |     |     |     |     | 215 |     |     |     |     | 220 |     |     |     |     |
| Lys | Arg | Ile | Lys | Met | Lys | Gln | Gly | Glu | Thr | Leu | Ala | Leu | Asn | Glu | Arg |
| 225 |     |     |     |     | 230 |     |     |     |     | 235 |     |     |     |     | 240 |
| Ile | Met | Leu | Ser | Leu | Val | Ser | Thr | Gly | Asp | Cys | Pro | Phe | Ile | Val | Cys |
|     |     |     |     | 245 |     |     |     |     | 250 |     |     |     |     | 255 |     |
| Met | Ser | Tyr | Ala | Phe | His | Thr | Pro | Asp | Lys | Leu | Ser | Phe | Ile | Leu | Asp |
|     |     |     | 260 |     |     |     |     | 265 |     |     |     |     | 270 |     |     |
| Leu | Met | Asn | Gly | Gly | Asp | Leu | His | Tyr | His | Leu | Ser | Gln | His | Gly | Val |
|     |     | 275 |     |     |     |     | 280 |     |     |     |     | 285 |     |     |     |
| Phe | Ser | Glu | Ala | Asp | Met | Arg | Phe | Tyr | Ala | Ala | Glu | Ile | Ile | Leu | Gly |
|     | 290 |     |     |     |     | 295 |     |     |     |     | 300 |     |     |     |     |
| Leu | Glu | His | Met | His | Asn | Arg | Phe | Val | Val | Tyr | Arg | Asp | Leu | Lys | Pro |
| 305 |     |     |     |     | 310 |     |     |     |     | 315 |     |     |     |     | 320 |
| Ala | Asn | Ile | Leu | Leu | Asp | Glu | His | Gly | His | Val | Arg | Ile | Ser | Asp | Leu |
|     |     |     |     | 325 |     |     |     |     | 330 |     |     |     |     | 335 |     |
| Gly | Leu | Ala | Cys | Asp | Phe | Ser | Lys | Lys | Lys | Pro | His | Ala | Ser | Val | Gly |
|     |     |     | 340 |     |     |     |     | 345 |     |     |     |     | 350 |     |     |
| Thr | His | Gly | Tyr | Met | Ala | Pro | Glu | Val | Leu | Gln | Lys | Gly | Val | Ala | Tyr |
|     |     | 355 |     |     |     |     | 360 |     |     |     |     | 365 |     |     |     |
| Asp | Ser | Ser | Ala | Asp | Trp | Phe | Ser | Leu | Gly | Cys | Met | Leu | Phe | Lys | Leu |
|     | 370 |     |     |     |     | 375 |     |     |     |     | 380 |     |     |     |     |
| Leu | Arg | Gly | His | Ser | Pro | Phe | Arg | Gln | His | Lys | Thr | Lys | Asp | Lys | His |
| 385 |     |     |     |     | 390 |     |     |     |     | 395 |     |     |     |     | 400 |
| Glu | Ile | Asp | Arg | Met | Thr | Leu | Thr | Met | Ala | Val | Glu | Leu | Pro | Asp | Ser |
|     |     |     |     | 405 |     |     |     |     | 410 |     |     |     |     | 415 |     |
| Phe | Ser | Pro | Glu | Leu | Arg | Ser | Leu | Leu | Glu | Gly | Leu | Leu | Gln | Arg | Asp |
|     |     |     | 420 |     |     |     |     | 425 |     |     |     |     | 430 |     |     |
| Val | Asn | Arg | Arg | Leu | Gly | Cys | Leu | Gly | Arg | Gly | Ala | Gln | Glu | Val | Lys |
|     |     | 435 |     |     |     |     | 440 |     |     |     |     | 445 |     |     |     |
| Glu | Ser | Pro | Phe | Phe | Arg | Ser | Leu | Asp | Trp | Gln | Met | Val | Phe | Leu | Gln |
|     | 450 |     |     |     |     | 455 |     |     |     |     | 460 |     |     |     |     |
| Lys | Tyr | Pro | Pro | Pro | Leu | Ile | Pro | Pro | Arg | Gly | Glu | Val | Asn | Ala | Ala |
| 465 |     |     |     |     | 470 |     |     |     |     | 475 |     |     |     |     | 480 |
| Asp | Ala | Phe | Asp | Ile | Gly | Ser | Phe | Asp | Glu | Glu | Asp | Thr | Lys | Gly | Ile |
|     |     |     |     | 485 |     |     |     |     | 490 |     |     |     |     | 495 |     |
| Lys | Leu | Leu | Asp | Ser | Asp | Gln | Glu | Leu | Tyr | Arg | Asn | Phe | Pro | Leu | Thr |
|     |     |     | 500 |     |     |     |     | 505 |     |     |     |     | 510 |     |     |
| Ile | Ser | Glu | Arg | Trp | Gln | Gln | Glu | Val | Ala | Glu | Thr | Val | Phe | Asp | Thr |
|     |     | 515 |     |     |     |     | 520 |     |     |     |     | 525 |     |     |     |
| Ile | Asn | Ala | Glu | Thr | Asp | Arg | Leu | Glu | Ala | Arg | Lys | Lys | Ala | Lys | Asn |
|     | 530 |     |     |     |     | 535 |     |     |     |     | 540 |     |     |     |     |
| Lys | Gln | Leu | Gly | His | Glu | Glu | Asp | Tyr | Ala | Leu | Gly | Lys | Asp | Cys | Ile |
| 545 |     |     |     |     | 550 |     |     |     |     | 555 |     |     |     |     | 560 |
| Met | His | Gly | Tyr | Met | Ser | Lys | Met | Gly | Asn | Pro | Phe | Leu | Thr | Gln | Trp |
|     |     |     |     | 565 |     |     |     |     | 570 |     |     |     |     | 575 |     |

```
Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Ala Asn Gly
            675                 680                 685

Leu
```

( 2 ) INFORMATION FOR SEQ ID NO:19:

( i ) SEQUENCE CHARACTERISTICS:
        ( A ) LENGTH: 688 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Lys Val
            20                  25                  30

Val Leu Pro Glu Pro Ser Ile Arg Ser Val Met Gln Arg Tyr Leu Ala
            35                  40                  45

Glu Arg Asn Glu Ile Thr Phe Asp Lys Ile Phe Asn Gln Lys Ile Gly
    50                  55                  60

Phe Leu Leu Phe Lys Asp Phe Cys Leu Asn Glu Ile Gly Glu Ala Val
65                  70                  75                  80

Pro Gln Val Lys Phe Tyr Glu Glu Ile Lys Glu Tyr Glu Lys Leu Asp
                85                  90                  95

Asn Glu Glu Asp Arg Leu His Arg Ser Arg Gln Met Tyr Asp Ala Tyr
            100                 105                 110

Ile Met Arg Glu Leu Leu Ser Ser Thr His Gln Phe Ser Lys Gln Ala
            115                 120                 125

Val Glu His Val Gln Ser His Leu Ser Lys Lys Gln Val Thr Pro Thr
    130                 135                 140

Leu Phe Gln Pro Tyr Ile Glu Glu Ile Cys Glu Ser Leu Arg Gly Asp
145                 150                 155                 160

Ile Phe Gln Lys Phe Met Glu Ser Glu Lys Phe Thr Arg Phe Cys Gln
                165                 170                 175

Trp Lys Asn Val Glu Leu Asn Ile His Leu Ser Met Asn Asp Phe Ser
            180                 185                 190

Val His Arg Ile Ile Gly Arg Gly Gly Phe Gly Glu Val Tyr Gly Cys
    195                 200                 205

Arg Lys Ala Asp Thr Gly Lys Met Tyr Ala Met Lys Cys Leu Asp Lys
    210                 215                 220

Lys Arg Val Lys Met Lys Gln Gly Glu Thr Leu Ala Leu Asn Glu Arg
225                 230                 235                 240
```

```
Ile Met Leu Ser Leu Val Ser Thr Gly Asp Cys Pro Phe Ile Val Cys
            245                 250                 255

Met Thr Tyr Ala Phe His Thr Pro Asp Lys Leu Cys Phe Ile Leu Asp
            260                 265                 270

Leu Met Asn Gly Gly Asp Met His Tyr His Leu Ser Gln His Gly Val
            275                 280                 285

Phe Ser Glu Lys Glu Met Arg Phe Tyr Ala Ser Glu Ile Ile Leu Gly
            290                 295                 300

Leu Glu His Met His Thr Cys Phe Val Val Tyr Arg Asp Leu Lys Pro
305                 310                 315                 320

Ala Asn Ile Leu Leu Asp Glu Tyr Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Thr Cys Tyr
            355                 360                 365

Asp Ser Ser Ala Asp Trp Phe Ser Leu Gly Cys Met Leu Phe Lys Leu
            370                 375                 380

Leu Arg Gly His Ser Pro Phe Arg Gln His Lys Thr Lys Asp Lys His
385                 390                 395                 400

Glu Ile Asp Arg Met Thr Leu Thr Val Asn Val Gln Leu Pro Asp Ala
                405                 410                 415

Phe Ser Pro Glu Leu Arg Ser Leu Leu Glu Gly Leu Leu Gln Arg Asp
            420                 425                 430

Val Ser Gln Arg Leu Gly Cys Tyr Gly Gly Gly Ala Arg Glu Leu Lys
            435                 440                 445

Glu His Ile Phe Phe Lys Gly Ile Asp Trp Gln Tyr Val Tyr Leu Arg
450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
            485                 490                 495

Lys Leu Leu Asp Cys Asp Gln Asp Leu Tyr Lys Asn Phe Pro Leu Met
            500                 505                 510

Ile Ser Glu Arg Trp Gln Gln Glu Val Val Glu Thr Ile Tyr Asp Ala
            515                 520                 525

Val Asn Ala Glu Thr Asp Lys Ile Glu Ala Arg Lys Lys Ala Lys Asn
            530                 535                 540

Lys Gln Leu Cys Gln Glu Glu Asp Tyr Ala Met Gly Lys Asp Cys Ile
545                 550                 555                 560

Met His Gly Tyr Met Leu Lys Leu Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ser Arg Gln Asn Leu Leu Thr Met Glu Gln Ile Met Ser
            595                 600                 605

Val Glu Glu Thr Gln Ile Lys Asp Arg Lys Cys Ile Leu Leu Arg Val
            610                 615                 620

Lys Gly Gly Lys Gln Phe Val Leu Gln Cys Glu Ser Asp Pro Glu Phe
625                 630                 635                 640

Ala Gln Trp Leu Lys Glu Leu Thr Cys Thr Phe Asn Glu Ala Gln Arg
                645                 650                 655

Leu Leu Arg Arg Ala Pro Lys Phe Leu Asn Lys Pro Arg Ala Ala Ile
            660                 665                 670
```

Leu  Glu  Phe  Ser  Lys  Pro  Pro  Leu  Cys  His  Arg  Asn  Ser  Ser  Gly  Leu
                    675                 680                      685

( 2 ) INFORMATION FOR SEQ ID NO:20:

( i ) SEQUENCE CHARACTERISTICS:
        ( A ) LENGTH: 699 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Met  Ala  Asp  Leu  Glu  Ala  Val  Leu  Ala  Asp  Val  Ser  Tyr  Leu  Met  Ala
 1                    5                   10                      15

Met  Glu  Lys  Ser  Lys  Cys  Thr  Pro  Ala  Ala  Arg  Ala  Ser  Lys  Lys  Leu
                20                      25                      30

Asn  Leu  Pro  Asp  Pro  Ser  Val  Arg  Ser  Val  Met  Tyr  Lys  Tyr  Leu  Glu
           35                      40                      45

Lys  Glu  Gly  Glu  Leu  Asn  Phe  His  Lys  Asn  Phe  Asn  Glu  Val  Leu  Gly
      50                     55                      60

Tyr  Leu  Leu  Phe  Lys  Asp  Phe  Cys  Glu  Asn  Asp  Ser  Glu  Glu  Pro  Ile
 65                      70                      75                      80

Gln  Gln  Leu  Lys  Phe  Phe  Glu  Gln  Ile  Lys  Leu  Phe  Glu  Lys  Thr  Glu
                     85                      90                      95

Cys  Tyr  Asp  Glu  Arg  Lys  Lys  Met  Ala  Arg  Asp  Ile  Tyr  Asp  Asn  Phe
                100                     105                     110

Ile  Met  Glu  Glu  Met  Leu  Ser  His  Thr  Tyr  Glu  Tyr  Ser  Lys  His  Ala
           115                     120                     125

Val  Ala  Ser  Val  Gln  Lys  Tyr  Leu  Leu  Lys  Asn  Glu  Val  Pro  Val  Asp
      130                     135                     140

Leu  Phe  Glu  Pro  Tyr  Leu  Glu  Glu  Ile  Phe  Thr  Gln  Leu  Lys  Gly  Lys
145                     150                     155                     160

Pro  Phe  Lys  Lys  Phe  Leu  Glu  Ser  Asp  Lys  Phe  Thr  Arg  Phe  Cys  Gln
                165                     170                     175

Trp  Lys  Asn  Leu  Glu  Leu  Asn  Ile  Gln  Leu  Thr  Met  Asn  Asp  Phe  Ser
           180                     185                     190

Val  His  Arg  Ile  Ile  Gly  Arg  Gly  Gly  Phe  Gly  Glu  Val  Tyr  Gly  Cys
      195                     200                     205

Arg  Lys  Ala  Asp  Thr  Gly  Lys  Met  Tyr  Ala  Met  Lys  Cys  Leu  Asp  Lys
210                     215                     220

Lys  Arg  Ile  Lys  Met  Lys  Gln  Gly  Glu  Met  Leu  Ala  Leu  Asn  Glu  Arg
225                     230                     235                     240

Asn  Met  Leu  Gln  Ala  Val  Ser  Thr  Gly  Ile  Asp  Cys  Pro  Phe  Ile  Val
                245                     250                     255

Cys  Met  Thr  Tyr  Ala  Phe  His  Thr  Pro  Asp  Lys  Leu  Cys  Phe  Ile  Leu
           260                     265                     270

Asp  Leu  Met  Asn  Gly  Gly  Asp  Leu  His  Tyr  His  Leu  Ser  Gln  His  Gly
      275                     280                     285

Ile  Phe  Ser  Glu  Asp  Glu  Met  Lys  Phe  Tyr  Ala  Ala  Glu  Val  Ile  Leu
290                     295                     300

Gly  Leu  Glu  His  Met  His  Lys  Arg  Cys  Ile  Val  Tyr  Arg  Asp  Leu  Lys
305                     310                     315                     320

Pro  Ala  Asn  Ile  Leu  Leu  Asp  Glu  Asn  Gly  His  Ile  Arg  Ile  Ser  Asp
                325                     330                     335

Leu  Gly  Leu  Ala  Cys  Asp  Phe  Ser  Lys  Lys  Lys  Pro  His  Ala  Ser  Val

|  |  |  | 340 |  |  |  |  | 345 |  |  |  |  | 350 |  |  |
|---|---|---|---|---|---|---|---|---|---|---|---|---|---|---|---|
| Gly | Thr | His<br>355 | Gly | Tyr | Met | Ala | Pro<br>360 | Glu | Val | Leu | Ser | Lys<br>365 | Gly | Thr | Ser |
| Tyr | Asp<br>370 | Ser | Cys | Ala | Asp | Trp<br>375 | Phe | Ser | Phe | Gly | Cys<br>380 | Met | Leu | Tyr | Lys |
| Leu<br>385 | Leu | Lys | Gly | His | Ser<br>390 | Pro | Phe | Arg | Gln | His<br>395 | Lys | Thr | Lys | Asp | Lys<br>400 |
| Leu | Glu | Ile | Asp | Lys<br>405 | Met | Thr | Leu | Thr | Met<br>410 | Asn | Val | Glu | Leu | Pro<br>415 | Glu |
| Ser | Phe | Ser | Leu<br>420 | Glu | Leu | Lys | Asn | Leu<br>425 | Leu | Glu | Met | Leu | Leu<br>430 | Gln | Arg |
| Asp | Val | Ser<br>435 | Lys | Arg | Leu | Gly | Cys<br>440 | Met | Gly | Asn | Gly | Ala<br>445 | Asp | Glu | Val |
| Lys | Met<br>450 | His | Asn | Phe | Phe | Cys<br>455 | Gly | Ile | Asp | Trp | His<br>460 | Gln | Val | Tyr | Ile |
| Gln<br>465 | Lys | Tyr | Thr | Pro | Pro<br>470 | Leu | Val | Pro | Pro | Arg<br>475 | Gly | Glu | Val | Asn | Ala<br>480 |
| Ala | Asp | Ala | Phe | Asp<br>485 | Ile | Gly | Ser | Phe | Asp<br>490 | Glu | Glu | Asp | Thr | Lys<br>495 | Gly |
| Ile | Lys | Leu | Asn<br>500 | Asp | Ala | Asp | Gln | Asp<br>505 | Leu | Tyr | Lys | Met | Phe<br>510 | Ser | Leu |
| Thr | Ile | Ser<br>515 | Glu | Arg | Trp | Gln | Gln<br>520 | Glu | Val | Ser | Glu | Thr<br>525 | Val | Phe | Asp |
| Thr | Val<br>530 | Asn | Thr | Glu | Thr | Asp<br>535 | Lys | Leu | Glu | Gln | Lys<br>540 | Arg | Lys | Leu | Lys |
| Gln<br>545 | Lys | Gln | His | Phe | Asp<br>550 | Ala | Asp | Glu | Lys | Glu<br>555 | Ser | Asp | Cys | Ile | Leu<br>560 |
| His | Gly | Tyr | Ile | Lys<br>565 | Lys | Leu | Gly | Gly | Ser<br>570 | Phe | Ala | Ser | Leu | Trp<br>575 | Gln |
| Thr | Lys | Tyr | Ala<br>580 | Lys | Leu | Tyr | Pro | Asn<br>585 | Arg | Leu | Glu | Leu | His<br>590 | Ser | Glu |
| Ser | Gly | Asn<br>595 | Asn | Lys | Pro | Glu | Leu<br>600 | Ile | Phe | Met | Asp | Gln<br>605 | Val | Glu | Asp |
| Ile | Ser<br>610 | Ser | Asp | Phe | Ile | Leu<br>615 | His | Lys | Asn | Glu | Asn<br>620 | Cys | Ile | Gln | Ile |
| Arg<br>625 | Ile | Asn | Asp | Gly | Thr<br>630 | Arg | Asp | Gly | Arg | Ile<br>635 | Ile | Leu | Thr | Asn | Ser<br>640 |
| Asp | Glu | Ile | Gly | Leu<br>645 | Lys | Glu | Trp | Ser | Ser<br>650 | Ser | Leu | Arg | Ser | Ala<br>655 | His |
| Lys | Ile | Ser | Gln<br>660 | Asp | Leu | Leu | Gly | Ser<br>665 | Met | Ala | Lys | Lys | Ala<br>670 | Gly | Lys |
| Ile | Tyr | Gly<br>675 | Ser | Glu | Arg | Asp | Val<br>680 | Asn | Lys | Ser | Met | Ile<br>685 | Phe | Gly | Gly |
| Asn | Cys<br>690 | Ser | Thr | Lys | Thr | Ser<br>695 | Asn | Gly | Ser | Asn |  |  |  |  |  |

( 2 ) INFORMATION FOR SEQ ID NO:21:

( i ) SEQUENCE CHARACTERISTICS:
        ( A ) LENGTH: 1983 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 13..1740

(xi) SEQUENCE DESCRIPTION: SEQ ID NO:21:

| | | | | | | | | | | | | | | | | |
|---|---|---|---|---|---|---|---|---|---|---|---|---|---|---|---|---|
| GCCGTGCAGC | CC | ATG | GAG | CTC | GAG | AAC | ATC | GTA | GCG | AAC | ACG | GGG | CTA | | | 48 |
| | | Met | Glu | Leu | Glu | Asn | Ile | Val | Ala | Asn | Thr | Gly | Leu | | | |
| | | 1 | | | | 5 | | | | | 10 | | | | | |
| CTC | AAG | GCC | CGG | GAA | GGT | GGT | GGC | GGG | AAT | CGT | AAA | GGC | AAG | AGC | AAG | 96 |
| Leu | Lys | Ala | Arg | Glu | Gly | Gly | Gly | Gly | Asn | Arg | Lys | Gly | Lys | Ser | Lys | |
| | | 15 | | | | | 20 | | | | | 25 | | | | |
| AAA | TGG | CGC | CAG | ATG | CTG | CAG | TTC | CCC | CAC | ATC | AGC | CAG | TGT | GAA | GAG | 144 |
| Lys | Trp | Arg | Gln | Met | Leu | Gln | Phe | Pro | His | Ile | Ser | Gln | Cys | Glu | Glu | |
| | | 30 | | | | 35 | | | | | 40 | | | | | |
| CTC | CGG | CTC | ACC | TTG | GAA | CGT | GAC | TAC | CAC | AGC | CTG | TGT | GAG | CGT | CAG | 192 |
| Leu | Arg | Leu | Thr | Leu | Glu | Arg | Asp | Tyr | His | Ser | Leu | Cys | Glu | Arg | Gln | |
| 45 | | | | | 50 | | | | | 55 | | | | | 60 | |
| TCC | ATT | GGG | CGC | CTG | TTA | TTA | TGT | GAG | TTC | TGC | GCT | ACG | AGG | CCT | GAG | 240 |
| Ser | Ile | Gly | Arg | Leu | Leu | Leu | Cys | Glu | Phe | Cys | Ala | Thr | Arg | Pro | Glu | |
| | | | | 65 | | | | | 70 | | | | | 75 | | |
| CTG | ACC | CGC | TGT | ACT | GCC | TTC | CTG | GAT | GGG | GTG | GCT | GAG | TAT | GAG | GTG | 288 |
| Leu | Thr | Arg | Cys | Thr | Ala | Phe | Leu | Asp | Gly | Val | Ala | Glu | Tyr | Glu | Val | |
| | | | 80 | | | | | 85 | | | | | 90 | | | |
| ACC | CCT | GAT | GAG | AAA | CGG | AAG | GCA | TGT | GGG | CGT | CGG | CTA | ATG | CAG | AAT | 336 |
| Thr | Pro | Asp | Glu | Lys | Arg | Lys | Ala | Cys | Gly | Arg | Arg | Leu | Met | Gln | Asn | |
| | | | 95 | | | | | 100 | | | | | 105 | | | |
| TTT | CTG | AGC | CAC | ACG | GGT | CCT | GAC | CTC | ATC | CCT | GAA | GTT | CCC | CGG | CAG | 384 |
| Phe | Leu | Ser | His | Thr | Gly | Pro | Asp | Leu | Ile | Pro | Glu | Val | Pro | Arg | Gln | |
| | | 110 | | | | | 115 | | | | | 120 | | | | |
| CTG | GTG | AGT | AAC | TGT | GCC | CAG | CGG | CTA | GAG | CAG | GGA | CCC | TGC | AAA | GAC | 432 |
| Leu | Val | Ser | Asn | Cys | Ala | Gln | Arg | Leu | Glu | Gln | Gly | Pro | Cys | Lys | Asp | |
| 125 | | | | | 130 | | | | | 135 | | | | | 140 | |
| CTC | TTC | CAG | GAG | CTG | ACC | CGG | CTG | ACC | CAT | GAG | TAC | CTA | AGC | ATG | GGC | 480 |
| Leu | Phe | Gln | Glu | Leu | Thr | Arg | Leu | Thr | His | Glu | Tyr | Leu | Ser | Met | Gly | |
| | | | | 145 | | | | | 150 | | | | | 155 | | |
| CCT | TTT | GGC | GAC | TAC | CTC | GAC | AGC | ATC | TAC | TTC | AAC | CGT | TTC | CTG | CAG | 528 |
| Pro | Phe | Gly | Asp | Tyr | Leu | Asp | Ser | Ile | Tyr | Phe | Asn | Arg | Phe | Leu | Gln | |
| | | | 160 | | | | | 165 | | | | | 170 | | | |
| TGG | AAG | TGG | CTG | GAA | AGG | CAG | CCA | GTG | ACC | AAA | AAC | ACC | TTT | AGG | CAG | 576 |
| Trp | Lys | Trp | Leu | Glu | Arg | Gln | Pro | Val | Thr | Lys | Asn | Thr | Phe | Arg | Gln | |
| | | 175 | | | | | 180 | | | | | 185 | | | | |
| TAC | CGA | GTC | CTG | GGC | AAA | GGT | GGC | TTT | GGG | GAG | GTG | TGT | GCC | TGC | CAG | 624 |
| Tyr | Arg | Val | Leu | Gly | Lys | Gly | Gly | Phe | Gly | Glu | Val | Cys | Ala | Cys | Gln | |
| | 190 | | | | | 195 | | | | | 200 | | | | | |
| GTG | CGG | ACA | ACA | GGC | AAG | ATG | TAT | GCG | TAC | AAA | AAC | TGG | AAA | AAG | AAA | 672 |
| Val | Arg | Thr | Thr | Gly | Lys | Met | Tyr | Ala | Tyr | Lys | Asn | Trp | Lys | Lys | Lys | |
| 205 | | | | | 210 | | | | | 215 | | | | | 220 | |
| CGA | ATA | AAG | AAG | CGG | AAG | GGG | GAG | GCC | ATG | TCT | CTC | AAC | GAG | AAG | CAG | 720 |
| Arg | Ile | Lys | Lys | Arg | Lys | Gly | Glu | Ala | Met | Ser | Leu | Asn | Glu | Lys | Gln | |
| | | | | 225 | | | | | 230 | | | | | 235 | | |
| ATC | CTG | GAG | AAA | GTG | AAC | AGT | AGG | TTT | GTA | GTG | ATC | TTA | GCC | TAC | GCA | 768 |
| Ile | Leu | Glu | Lys | Val | Asn | Ser | Arg | Phe | Val | Val | Ile | Leu | Ala | Tyr | Ala | |
| | | | 240 | | | | | 245 | | | | | 250 | | | |
| TAT | GAG | ACC | AAG | GAT | GCA | CTG | TGC | CTG | GTG | CTG | ACA | TTG | ATG | AAT | GGA | 816 |
| Tyr | Glu | Thr | Lys | Asp | Ala | Leu | Cys | Leu | Val | Leu | Thr | Leu | Met | Asn | Gly | |
| | | 255 | | | | | 260 | | | | | 265 | | | | |
| GGC | GAC | CTC | AAG | TTC | CAC | ATC | TAC | CAC | ATG | GGC | CAG | GCT | GGC | TTT | CCC | 864 |
| Gly | Asp | Leu | Lys | Phe | His | Ile | Tyr | His | Met | Gly | Gln | Ala | Gly | Phe | Pro | |
| | | 270 | | | | | 275 | | | | | 280 | | | | |
| GAA | GCA | CGT | GCT | GTG | TTC | TAT | GCT | GCC | GAG | ATC | TGC | TGT | GGT | CTG | GAG | 912 |
| Glu | Ala | Arg | Ala | Val | Phe | Tyr | Ala | Ala | Glu | Ile | Cys | Cys | Gly | Leu | Glu | |
| 285 | | | | | 290 | | | | | 295 | | | | | 300 | |

| | | | | | | | | | | | | | | | | |
|---|---|---|---|---|---|---|---|---|---|---|---|---|---|---|---|---|
| GAC | TTA | CAC | CGG | GAA | CGC | ATC | GTG | TAC | AGG | GAC | CTA | AAG | CCA | GAG | AAT | 960 |
| Asp | Leu | His | Arg | Glu | Arg | Ile | Val | Tyr | Arg | Asp | Leu | Lys | Pro | Glu | Asn | |
| | | | | 305 | | | | 310 | | | | | 315 | | | |
| ATC | CTT | CTG | GAT | GAC | CAT | GGC | CAC | ATT | CGA | ATC | TCC | GAC | CTG | GGC | CTG | 1008 |
| Ile | Leu | Leu | Asp | Asp | His | Gly | His | Ile | Arg | Ile | Ser | Asp | Leu | Gly | Leu | |
| | | | 320 | | | | | 325 | | | | 330 | | | | |
| GCT | GTG | CAT | GTT | CCT | GAG | GGC | CAG | ACC | ATC | AAA | GGC | CGT | GTG | GGC | ACT | 1056 |
| Ala | Val | His | Val | Pro | Glu | Gly | Gln | Thr | Ile | Lys | Gly | Arg | Val | Gly | Thr | |
| | | 335 | | | | | 340 | | | | | 345 | | | | |
| GTG | GGC | TAC | ATG | GCT | CCA | GAG | GTG | GTG | AAG | AAT | GAG | CGC | TAC | ACA | TTC | 1104 |
| Val | Gly | Tyr | Met | Ala | Pro | Glu | Val | Val | Lys | Asn | Glu | Arg | Tyr | Thr | Phe | |
| | 350 | | | | | 355 | | | | | 360 | | | | | |
| AGT | CCT | GAC | TGG | TGG | GCG | CTA | GGC | TGC | CTC | CTG | TAC | GAG | ATG | ATT | GCG | 1152 |
| Ser | Pro | Asp | Trp | Trp | Ala | Leu | Gly | Cys | Leu | Leu | Tyr | Glu | Met | Ile | Ala | |
| 365 | | | | | 370 | | | | 375 | | | | | 380 | | |
| GGA | CAG | TCG | CCC | TTC | CAG | CAG | AGG | AAG | AAG | AAG | ATC | AAG | CGG | GAG | GAG | 1200 |
| Gly | Gln | Ser | Pro | Phe | Gln | Gln | Arg | Lys | Lys | Lys | Ile | Lys | Arg | Glu | Glu | |
| | | | | 385 | | | | | 390 | | | | | 395 | | |
| GTG | GAG | CGG | CTG | GTC | AAG | GAG | GTG | GCT | GAG | GAG | TAC | ACC | GAC | CGC | TTC | 1248 |
| Val | Glu | Arg | Leu | Val | Lys | Glu | Val | Ala | Glu | Glu | Tyr | Thr | Asp | Arg | Phe | |
| | | | 400 | | | | | 405 | | | | | 410 | | | |
| TCC | CCA | CAG | GCA | CGC | TCA | CTC | TGT | TCT | CAG | CTT | CTC | AAC | AAG | GAC | CCT | 1296 |
| Ser | Pro | Gln | Ala | Arg | Ser | Leu | Cys | Ser | Gln | Leu | Leu | Asn | Lys | Asp | Pro | |
| | | 415 | | | | | 420 | | | | | 425 | | | | |
| GCT | GAG | CGC | CTG | GGG | TGT | CGT | GGA | GGT | GGT | GCC | CGT | GAG | GTA | AAG | GAG | 1344 |
| Ala | Glu | Arg | Leu | Gly | Cys | Arg | Gly | Gly | Gly | Ala | Arg | Glu | Val | Lys | Glu | |
| | 430 | | | | | 435 | | | | | 440 | | | | | |
| CAC | CCC | CTT | TTC | AAG | AAA | CTG | AAT | TTC | AAG | CGG | CTG | GGA | GCT | GGA | ATG | 1392 |
| His | Pro | Leu | Phe | Lys | Lys | Leu | Asn | Phe | Lys | Arg | Leu | Gly | Ala | Gly | Met | |
| 445 | | | | | 450 | | | | | 455 | | | | | 460 | |
| CTA | GAA | CCA | CCT | TTT | AAA | CCT | GAC | CCC | CAG | GCC | ATT | TAC | TGC | AAG | GAC | 1440 |
| Leu | Glu | Pro | Pro | Phe | Lys | Pro | Asp | Pro | Gln | Ala | Ile | Tyr | Cys | Lys | Asp | |
| | | | | 465 | | | | | 470 | | | | | 475 | | |
| GTG | CTG | GAC | ATT | GAA | CAG | TTC | TCC | ACA | GTT | AAA | GGT | GTG | GAT | CTG | GAG | 1488 |
| Val | Leu | Asp | Ile | Glu | Gln | Phe | Ser | Thr | Val | Lys | Gly | Val | Asp | Leu | Glu | |
| | | | 480 | | | | | 485 | | | | | 490 | | | |
| CCC | ACA | GAC | CAA | GAC | TTC | TAC | CAG | AAG | TTT | GCC | ACG | GGT | AGT | GTG | TCC | 1536 |
| Pro | Thr | Asp | Gln | Asp | Phe | Tyr | Gln | Lys | Phe | Ala | Thr | Gly | Ser | Val | Ser | |
| | | 495 | | | | | 500 | | | | | 505 | | | | |
| ATC | CCC | TGG | CAG | AAC | GAG | ATG | GTG | GAG | ACT | GAG | TGC | TTC | CAG | GAA | CTA | 1584 |
| Ile | Pro | Trp | Gln | Asn | Glu | Met | Val | Glu | Thr | Glu | Cys | Phe | Gln | Glu | Leu | |
| | 510 | | | | | 515 | | | | | 520 | | | | | |
| AAT | GTC | TTT | GGG | CTG | GAT | GGG | TCT | GTT | CCC | CCA | GAC | CTG | GAC | TGG | AAG | 1632 |
| Asn | Val | Phe | Gly | Leu | Asp | Gly | Ser | Val | Pro | Pro | Asp | Leu | Asp | Trp | Lys | |
| 525 | | | | | 530 | | | | | 535 | | | | | 540 | |
| GGC | CAG | CCC | ACT | GCA | CCC | CCC | AAG | AAG | GGA | TTG | CTA | CAG | AGA | CTC | TTC | 1680 |
| Gly | Gln | Pro | Thr | Ala | Pro | Pro | Lys | Lys | Gly | Leu | Leu | Gln | Arg | Leu | Phe | |
| | | | | 545 | | | | | 550 | | | | | 555 | | |
| AGT | AGA | CAA | GAT | TGC | TGT | GGG | AAC | TGC | AGC | GAC | AGT | GAA | GAA | GAG | CTC | 1728 |
| Ser | Arg | Gln | Asp | Cys | Cys | Gly | Asn | Cys | Ser | Asp | Ser | Glu | Glu | Glu | Leu | |
| | | | 560 | | | | | 565 | | | | | 570 | | | |
| CCC | ACC | CGC | CTC | TAGCCCCCAG | GCCGAGGCCC | CCACCGGCGG | CTGGCGGTAG | | | | | | | | | 1780 |
| Pro | Thr | Arg | Leu | | | | | | | | | | | | | |
| | | 575 | | | | | | | | | | | | | | |

CAGCTACTCA GTGACTGACG TTGACAGTTT TGCACAGTGC TGTTTCCAGT TGTCCACGCC       1840

AGTCGTGGTC TGTGGAACAC AGCCGGAACT GTCCCCAGTG TCCTCCGTTC CTCAGCCACT       1900

GGCCCAGCTT GAGTATGACG AGGCCTGGGC CATCTTGGGA CAAAGGTGCG TCCCTTCAGC       1960

TCTTCTCTGT GGAGCTCGGG GCG                                              1983

( 2 ) INFORMATION FOR SEQ ID NO:22:

( i ) SEQUENCE CHARACTERISTICS:
        ( A ) LENGTH: 576 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met Glu Leu Glu Asn Ile Val Ala Asn Thr Gly Leu Leu Lys Ala Arg
 1               5                  10                  15
Glu Gly Gly Gly Gly Asn Arg Lys Gly Lys Ser Lys Lys Trp Arg Gln
                20                  25                  30
Met Leu Gln Phe Pro His Ile Ser Gln Cys Glu Glu Leu Arg Leu Thr
            35                  40                  45
Leu Glu Arg Asp Tyr His Ser Leu Cys Glu Arg Gln Ser Ile Gly Arg
        50                  55                  60
Leu Leu Leu Cys Glu Phe Cys Ala Thr Arg Pro Glu Leu Thr Arg Cys
65                  70                  75                  80
Thr Ala Phe Leu Asp Gly Val Ala Glu Tyr Glu Val Thr Pro Asp Glu
                85                  90                  95
Lys Arg Lys Ala Cys Gly Arg Arg Leu Met Gln Asn Phe Leu Ser His
            100                 105                 110
Thr Gly Pro Asp Leu Ile Pro Glu Val Pro Arg Gln Leu Val Ser Asn
        115                 120                 125
Cys Ala Gln Arg Leu Glu Gln Gly Pro Cys Lys Asp Leu Phe Gln Glu
    130                 135                 140
Leu Thr Arg Leu Thr His Glu Tyr Leu Ser Met Gly Pro Phe Gly Asp
145                 150                 155                 160
Tyr Leu Asp Ser Ile Tyr Phe Asn Arg Phe Leu Gln Trp Lys Trp Leu
                165                 170                 175
Glu Arg Gln Pro Val Thr Lys Asn Thr Phe Arg Gln Tyr Arg Val Leu
            180                 185                 190
Gly Lys Gly Gly Phe Gly Glu Val Cys Ala Cys Gln Val Arg Thr Thr
        195                 200                 205
Gly Lys Met Tyr Ala Tyr Lys Asn Trp Lys Lys Arg Ile Lys Lys
    210                 215                 220
Arg Lys Gly Glu Ala Met Ser Leu Asn Glu Lys Gln Ile Leu Glu Lys
225                 230                 235                 240
Val Asn Ser Arg Phe Val Val Ile Leu Ala Tyr Ala Tyr Glu Thr Lys
                245                 250                 255
Asp Ala Leu Cys Leu Val Leu Thr Leu Met Asn Gly Gly Asp Leu Lys
            260                 265                 270
Phe His Ile Tyr His Met Gly Gln Ala Gly Phe Pro Glu Ala Arg Ala
        275                 280                 285
Val Phe Tyr Ala Ala Glu Ile Cys Cys Gly Leu Glu Asp Leu His Arg
    290                 295                 300
Glu Arg Ile Val Tyr Arg Asp Leu Lys Pro Glu Asn Ile Leu Leu Asp
305                 310                 315                 320
Asp His Gly His Ile Arg Ile Ser Asp Leu Gly Leu Ala Val His Val
                325                 330                 335
Pro Glu Gly Gln Thr Ile Lys Gly Arg Val Gly Thr Val Gly Tyr Met
            340                 345                 350
Ala Pro Glu Val Val Lys Asn Glu Arg Tyr Thr Phe Ser Pro Asp Trp
```

|     | 355 |     |     |     |     | 360 |     |     |     |     | 365 |     |     |     |
|-----|-----|-----|-----|-----|-----|-----|-----|-----|-----|-----|-----|-----|-----|-----|
| Trp | Ala | Leu | Gly | Cys | Leu | Leu | Tyr | Glu | Met | Ile | Ala | Gly | Gln | Ser | Pro |
|     | 370 |     |     |     |     | 375 |     |     |     |     | 380 |     |     |     |
| Phe | Gln | Gln | Arg | Lys | Lys | Lys | Ile | Lys | Arg | Glu | Glu | Val | Glu | Arg | Leu |
| 385 |     |     |     |     | 390 |     |     |     |     | 395 |     |     |     |     | 400 |
| Val | Lys | Glu | Val | Ala | Glu | Glu | Tyr | Thr | Asp | Arg | Phe | Ser | Pro | Gln | Ala |
|     |     |     |     | 405 |     |     |     |     | 410 |     |     |     |     | 415 |
| Arg | Ser | Leu | Cys | Ser | Gln | Leu | Leu | Asn | Lys | Asp | Pro | Ala | Glu | Arg | Leu |
|     |     |     | 420 |     |     |     |     | 425 |     |     |     |     | 430 |     |
| Gly | Cys | Arg | Gly | Gly | Gly | Ala | Arg | Glu | Val | Lys | Glu | His | Pro | Leu | Phe |
|     |     | 435 |     |     |     |     | 440 |     |     |     |     | 445 |     |     |
| Lys | Lys | Leu | Asn | Phe | Lys | Arg | Leu | Gly | Ala | Gly | Met | Leu | Glu | Pro | Pro |
|     | 450 |     |     |     |     | 455 |     |     |     |     | 460 |     |     |     |
| Phe | Lys | Pro | Asp | Pro | Gln | Ala | Ile | Tyr | Cys | Lys | Asp | Val | Leu | Asp | Ile |
| 465 |     |     |     |     | 470 |     |     |     |     | 475 |     |     |     |     | 480 |
| Glu | Gln | Phe | Ser | Thr | Val | Lys | Gly | Val | Asp | Leu | Glu | Pro | Thr | Asp | Gln |
|     |     |     |     | 485 |     |     |     |     | 490 |     |     |     |     | 495 |
| Asp | Phe | Tyr | Gln | Lys | Phe | Ala | Thr | Gly | Ser | Val | Ser | Ile | Pro | Trp | Gln |
|     |     |     | 500 |     |     |     |     | 505 |     |     |     |     | 510 |     |
| Asn | Glu | Met | Val | Glu | Thr | Glu | Cys | Phe | Gln | Glu | Leu | Asn | Val | Phe | Gly |
|     |     | 515 |     |     |     |     | 520 |     |     |     |     | 525 |     |     |
| Leu | Asp | Gly | Ser | Val | Pro | Pro | Asp | Leu | Asp | Trp | Lys | Gly | Gln | Pro | Thr |
|     | 530 |     |     |     |     | 535 |     |     |     |     | 540 |     |     |     |
| Ala | Pro | Pro | Lys | Lys | Gly | Leu | Leu | Gln | Arg | Leu | Phe | Ser | Arg | Gln | Asp |
| 545 |     |     |     |     | 550 |     |     |     |     | 555 |     |     |     |     | 560 |
| Cys | Cys | Gly | Asn | Cys | Ser | Asp | Ser | Glu | Glu | Glu | Leu | Pro | Thr | Arg | Leu |
|     |     |     |     | 565 |     |     |     |     | 570 |     |     |     |     | 575 |

( 2 ) INFORMATION FOR SEQ ID NO:23:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

ATTTCTAGAA TTCGTTTCCT GCAGTGGAAG TGG      33

( 2 ) INFORMATION FOR SEQ ID NO:24:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

ATTAAGCTTT TAGTGATGGT GATGGTGATG CGGCTCCAGC ATGCCAGC      48